US007153977B2

(12) United States Patent
Lee

(10) Patent No.: US 7,153,977 B2
(45) Date of Patent: Dec. 26, 2006

(54) LIGANDS AND METHODS FOR PREPARING SAME

(75) Inventor: Chee Wee Lee, Singapore (SG)

(73) Assignee: National University of Singapore, Singapore (SG)

( * ) Notice: Subject to any disclaimer, the term of this patent is extended or adjusted under 35 U.S.C. 154(b) by 265 days.

(21) Appl. No.: 10/741,200

(22) Filed: Dec. 19, 2003

(65) Prior Publication Data

US 2004/0132981 A1 Jul. 8, 2004

Related U.S. Application Data

(62) Division of application No. 09/770,849, filed on Jan. 26, 2001, now abandoned.

(60) Provisional application No. 60/178,756, filed on Jan. 28, 2000.

(51) Int. Cl.
*A61K 31/405* (2006.01)
*C07D 209/16* (2006.01)

(52) U.S. Cl. .................. 548/504; 514/415; 514/419; 435/4; 435/7.1; 548/490

(58) Field of Classification Search .................. None
See application file for complete search history.

(56) References Cited

U.S. PATENT DOCUMENTS

| 4,366,241 A | 12/1982 | Tom et al. |
| 4,843,000 A | 6/1989 | Litman et al. |
| 4,849,338 A | 7/1989 | Litman et al. |
| 4,879,220 A | 11/1989 | Mrsny et al. |
| 4,966,891 A | 10/1990 | Fujiu et al. |
| 5,134,071 A | 7/1992 | Gaetjens |
| 5,227,487 A | 7/1993 | Haugland et al. |
| 5,274,113 A | 12/1993 | Kang et al. |
| 5,298,508 A | 3/1994 | Jacobson et al. |
| 5,326,692 A | 7/1994 | Brinkley et al. |
| 5,329,028 A | 7/1994 | Ashkenazi et al. |
| 5,367,058 A | 11/1994 | Pitner et al. |
| 5,405,864 A | 4/1995 | Broka |
| 5,405,975 A | 4/1995 | Kuhn et al. |
| 5,433,896 A | 7/1995 | Kang et al. |
| 5,442,045 A | 8/1995 | Haugland et al. |
| 5,451,663 A | 9/1995 | Kang et al. |
| 5,453,517 A | 9/1995 | Kuhn et al. |
| 5,459,276 A | 10/1995 | Kuhn et al. |
| 5,470,948 A | 11/1995 | Fahrenholz et al. |
| 5,516,864 A | 5/1996 | Kuhn et al. |
| 5,573,909 A | 11/1996 | Singer et al. |
| 5,648,270 A | 7/1997 | Kuhn et al. |
| 5,658,940 A | 8/1997 | Muller et al. |
| 5,688,941 A | 11/1997 | Cook et al. |
| 5,723,218 A | 3/1998 | Haugland et al. |
| 5,849,482 A | 12/1998 | Meyer, Jr. et al. |
| 5,998,603 A | 12/1999 | Cook et al. |
| 6,087,502 A | 7/2000 | Sato |
| 6,147,195 A | 11/2000 | Scherz et al. |
| 6,153,737 A | 11/2000 | Manoharan et al. |

FOREIGN PATENT DOCUMENTS

| DE | 40 14540 | 11/1991 |
| EP | 0 306 943 | 3/1989 |
| EP | 0 490 434 | 6/1992 |
| WO | WO 90/11779 | 10/1990 |
| WO | WO 91/00289 | 1/1991 |
| WO | WO 93/06121 | 4/1993 |
| WO | WO 95/02604 | 1/1995 |
| WO | WO 97/10847 | 3/1997 |
| WO | WO 97/20563 | 6/1997 |
| WO | WO 98/03632 | 1/1998 |
| WO | WO 98/11437 | 3/1998 |
| WO | WO 99/64396 | 12/1999 |

OTHER PUBLICATIONS

Erspamer, Vittorio (1966). "Occurrence of indolealkylamines in nature" Chapter 4, in Handbook of Experimental Pharmacology. Vol. XIX. 5-hydroxytryptamine and Related Indolealkylamines. Eichler and Farah, ed., Srpinger-Verlag: Berlin, pp. 132-181.*
Agbanyo, Francisca R. et al. (1990). "5'-S-(2-aminoethyl)-$N^6$-(4-nitrobenzyl)-5'-thioadenosine (SAENTA), a novel ligand with high affinity for polypeptides associated with nucleoside transport" *Biochem. J.* 270:605-614.
Baindur, Nandkishore and Neumeyer, John L. (1998). "A photoaffinity label for the D-1 dopamine receptor, (RS)-7[$^{125}$I]iodo-8-hydroxy-3-methyl-1-(4'-azido-phenyl)-2,3,4,5-tetrahydro-1H-3-benzazepine, selectively identifies the ligand binding subunits of the receptor" *J. Med. Chem.* 31:2069-2071.
Beasley, Charles M. et al. (1992). "Fluoxetine: a review of receptor and functional effects and their clinical implications" *Psychopharmacology* 107:1-10.
Belt, Judith A. (1983). "Nitrobenzylthioinosine-insensitive uridine transport in human lymphoblastoid and murine leukemia cells" *Biochem. Biophys. Res. Commun.* 110(2):417-423.
Belt, Judith A. (1983). "Heterogeneity of nucleoside transport in mammalian cells. Two types of transport activity in L1210 and other cultured neoplastic cells" *Mol. Pharmacol.* 24:479-484.
Belt, Judith A. and Noel, L. Diane (1985). "Nucleoside transport in Walker 256 rat carcinosarcoma and S49 mouse lymphoma cells" *Biochem. J.* 232:681-688.
Bolden-Watson, C., and Richelson, E. (1993). "Blockade by newly-developed antidepressants of biogenic amine uptake into rat brain synaptosomes" *Life Sciences* 52:1023-1029.

(Continued)

*Primary Examiner*—Jon Epperson
(74) *Attorney, Agent, or Firm*—Morrison & Foerster LLP

(57) ABSTRACT

A process is disclosed for modifying a parent ligand by attaching to the parent ligand a conjugation agent that is reactive with a moiety of a target receptor to which the parent ligand binds such that a covalent bond is formable between the conjugation agent and the receptor moiety. Also disclosed are compositions, probes and methods of detecting and/or quantifying receptors using the modified ligands of the invention.

3 Claims, 23 Drawing Sheets

OTHER PUBLICATIONS

Boyd, N.D. et al. (1991). "Photoaffinity labeling the substance P receptor using a derivative of substance P containing p-benzoylphenylalanine" *Biochemistry* 30:336-342.

Burgermeister, Wolfgang et al. (1982). "Photoaffinity labeling of the β-adrenergic receptor with azide derivatives of iodocyanopindolol" *J. Biol. Chem.* 257(8):5306-5311.

Cowen, P. J. and Anderson, I.M. (1991). "Abnormal 5-HT neuroendocrine function in depression: association or artifact?" Chapter 11 in *5-Hydroxytryptamine in Psychiatry*. Sandler et al. eds., Oxford University Press: New York, pp. 124-142.

Crawford, Charles R. et al. (1998). "Cloning of the human equilibrative, nitrobenzylmercaptopurine riboside (NBMPR)-insensitive nucleoside transporter ei by functional expression in a transport-deficient cell line" *J. Biol. Chem.* 273(9):5288-5293.

Curtin, N.J. et al. (1999). "Potentiation of the cytotoxicity of thymidylate synthase (TS) inhibitors by dipyridamole analogues with reduced $\alpha_1$-acid glycoprotein binding" *Brit. J. Cancer* 80(11):1738-1746.

Dallery, Nathalie et al. (1993). "Purification and functional chaeacterization of the ligand-binding domain from the retinoic acid receptor α: Evidence that sulfhydryl groups are involved in ligand-receptor interactions" *Biochemistry* 32:12428-12436.

Decristoforo, Clemens and Mather, Stephen J. (1999). "Technetium-99m somatostatin analogues: effect of labelling methods and peptide sequence" *Eur. J. Nucl. Med.* 26(8):869-876.

Derkach, V. et al. (1989). "$5-HT_3$ receptors are membrane ion channels" *Nature* 339:706-709.

Ehlert, Frederick J. and Griffin, Michael T. (1998). "The use of irreversible ligands to inactivate receptor subtypes: 4-DAMP mustard and muscarinic receptors in smooth muscle" *Life Sciences* 62(17/18):1659-1664.

Emerit, M.B. et al. (1985). "Irreversible blockade of central 5-HT binding sites by 8-methoxy-2'-chloro-pat" *Biochemical Pharmacology* 34(6):883-892.

Emerit, M.B. et al. (1986). "Irreversible blockade of central $5-HT_{1A}$ receptor binding sites by the photoaffinity probe 8-methoxy-3'-NAP-amino-PAT" *Eur. J. Pharm.* 127:67-81.

Emerit, M.B. et al. (1987). "Identification of the $5-HT_{1A}$ receptor binding subunit in rat brain membranes using the photoaffinity probe [$^3$H]8-methoxy-2-[N-n-propyl, N-3-(2-nitro-4-azidophenyl)aminopropyl]aminotetralin" *J. Neurochem.* 49(2):373-380.

Erspamer, Vittorio (1966). "Occurrence of idolealkylamines in nature" Chapter 4 in *Handbook of Experimental Pharmacology. Vol. XIX. 5-Hydroxytryptamine and Related Indolealkylamines*. Eichler and Farah, eds., Springer-Verlag: Berlin, pp. 132-181.

Fancy, David A. et al. (1996). "New chemistry for the study of multiprotein complexes: the six-histidine tag as a receptor for a protein crosslinking reagent" *Chem. & Biol.* 3(7):551-559.

Gati, W.P. et al. (1983). "Interaction of 2'-halogeno-2'-deoxyuridines with the human erythrocyte nucleoside transport mechanism" *Mol. Pharmacol.* 23:146-152.

Gati, Wendy P. et al. (1987). "[$^{125}$I]Iodohydroxynitrobenzylthioinosine: a new high-affinity nucleoside transporter probe" *Biochem. Cell Biol.* 65:467-473.

Goh, Lay-Beng et al. (1995). "Nitrobenzylthioinosine-binding protein overexpression in human breast, liver, stomach and colorectal tumour tissues" *Anticancer Res.* 15:2575-2579.

Gozlan, H. et al. (1987). "Photoaffinity labelling and solubilization of the central $5-HT_{1A}$ receptor binding site" *J. Receptor Res.* 7(1-4):195-221.

Griffith, Douglas A. and Jarvis, Simon M. (1996). "Nucleoside and nucleobase transport systems of mammalian cells" *Biochim. Biophys. Acta* 1286:153-181.

He, Xiaolan et al. (1995). "High-yield affinity alkylation of the atrial natriuretic factor receptor binding site" *Bioconjugate Chem.* 6:541-548.

Isambert, Marie-Francoise et al. (1998). "Photoaffinity labeling of the monoamine transporter of bovine chromaffin granules and other monoamine storage vesicles using 7-azido-8-[$^{125}$I]iodoketanserin" *Biochemistry* 28:2265-2270.

Kline, Toni B. et al. (1990). "Novel [(diazomethyl)carbonyl]-1,2,3,4-tetrahydronaphthalene derivatives as potential photoaffinity ligands for the $5-HT_{1A}$ receptor" *J. Med. Chem.* 33:950-955.

Koe, B. Kenneth (1990). "Preclinical pharmacology of sertraline: A potent and specific inhibitor of serotonin reuptake" *J. Clin. Psychiatry* 51:12 (suppl B):13-17.

Kurlander, Roger and Niedel, James (1985). "Affinity labeling of the Fc receptor on human monocytes using bifunctional cross-linking agents" *J. Immunol. Meth.* 78:247-258.

Lee, Chee Wee and Jarvis, Simon M. (1988). "Nucleoside transport in rat cerebral-cortical synaptosomes" *Biochem. J.* 249:557-564.

Lee, Chee Wee (1994). "Decrease in equilibrative uridine transport during monocytic differentiation of HL-60 leukaemia: involvement of protein kinase C" *Biochem. J.* 300:407-412.

Lee, Chee-Wee et al. (1995). "Sensitivity to inhibition by N-ethylmaleimide: a property of nitrobenzylthioinosine-sensitive equilibrative nucleoside transporter of murine myeloma cells" *Biochim. Biophys. Acta* 1268:200-208.

Li, Hanzhong et al. (1996). "Identification of the site in the substance P (NK-1) receptor for modulation of peptide binding by sulfhydryl reagents" *J. Biol. Chem.* 271(4):1950-1956.

Liu, Shuang and Edwards, D.Scott (2001). "Bifunctional chelators for therapeutic lanthanide radiopharmaceuticals" *Bioconjugate Chem.* 12:7-34.

Mahon, Anne C. and Hartig, Paul R. (1982). "Photolabeling of brain membrane proteins by lysergic acid diethylamide" *Life Sciences* 30:1179-1183.

Newman, Amy Hauck (1991). "Irreversible ligands as probes for drug receptors" in *Emerging Technologies and New Directions in Drug Abuse Research*. Rapaka et al. eds., Natl. Inst. Drug Abuse, pp. 256-283.

Noller, C.R. (1965). *Chemistry of Organic Compounds* London: W.B. Saunders Company p. 339.

Osses, Nelson et al. (1996). "Hypoxanthine enters human vascular endothelial cells (ECV 304) via the nitrobenzylthioinosine-insensitive equilibrative nucleoside transporter" *Biochem. J.* 317:843-848.

Paalman, S.R. et al. (1997). "Formation of a Covalent Complex Between Methylguanine Methyltransferase and DNA via Disulfide Bond Formation Between the Active Site Cysteine and a Thiol-Containing Analog of Guanine," *Nucleic Acids Research* 25(9):1795-1801.

Paterson, Alan R.P. et al. (1977). "Inhibition by nitrobenzylthioinosine of adenosine uptake by asynchronous HeLa cells" *Mol. Pharmacol.* 13:1147-1158.

Pávó, Imre et al. (1993). "Synthesis and binding characteristics of two sulfhydryl-reactive probes for vasopressin receptors" *FEBS* 316(1):59-62.

Peroutka, Stephen J. (1995). "Serotonin receptor subtypes: Their evolution and clinical relevance" *CNS Drugs* 4(Suppl 1):18-28.

Plagemann, Peter G.W. and Richey, David P. (1974). "Transport of nucleosides, nucleic acid bases, choline and glucose by animal cells in culture" *Biochim. Biophs. Acta* 344:263-305.

Plagemann, Peter G.W. et al. (1978). "Uridine transport in Novikoff rat hepatoma cells and other cell lines and its relationship to uridine phosphorylation and phosphorolysis" *J. Cell. Physiol.* 97:49-72.

Plagemann, Peter G.W. and Wohlhueter, Robert M. (1980). "Permeation of nucleosides, nucleic acid bases, and nucleotides in animal cells" in *Current Topics in Membrannes and Transport*. Bronner and Kleinzeller eds., Academic Press: New York, vol. 14, pp. 225-330.

Poznansky, Mark J. and Juliano, Rudolph L. (1984). "Biological approaches to the controlled delivery of drugs: A critical review" *Pharm. Rev.* 36(4):277-336.

Ransom, Richard W. et al. (1985). "A trifluoromethylphenyl piperazine drivative with high affinity for 5-hydroxytryptamine-1A sites in rat brain" *J. Neurochem.* 44(3):875-880.

Ransom, Richard W. et al. (1986). "Photoaffinity labeling of the 5-hydroxytryptamine $_{1A}$ receptor in rat hippocampus" *J. Neurochem.* 47(4):1066-1072.

Raymond, John R. et al. (1989). "Identification of the ligand-binding subunit of the human 5-hydroxytryptamine$_{1A}$ receptor with $N$-(p-azido-m-[$^{125}$I]iodophenethyl)spiperone, a high affinity radioiodinated photoaffinity probe" *Molecular Pharm.* 36:15-21.

Rudolf, Bogna et al. (1998). "Metallo-carbonyl complexes based on the CpFe(CO)$_2$($\eta^1$-N-imidato) system as protein labelling reagents: reactivity and selectivity studies using bovine serum albumin as a model protein" *New J. Chem.* pp. 813-818.

Šator, Vesna et al. (1978). "$N$-(3-pyrene)maleimide: A fluorescent probe of acetylchline receptor-Triton X-100 aggregates" *Archiv. Biochem. Biophys.* 190(1):57-66.

Shryoc, John C. and Belardinelli, Luiz (1997). "Adenosine and adenosine receptors in the cardiovascular system: Biochemistry, physiology and pharmacology" *Amer. J. Cardiol.* 79(12A):2-10.

Sullivan, Deirdre A. and Cohen, Jonathan B. (2000). "Mapping the agonist binding site of the nicotinic acetylcholine receptor" *J. Biol. Chem.* 275(17):12651-12660.

Swamy, Narasimha et al. (1997). "Identification of the subdomain in the nuclear receptor for the hormonal form of vitamin D$_3$, 1α, 25-dihydroxyvitamin D$_3$, vitamin D receptor, that is covalently modified by an affinity labeling reagent" *Arch. Biochem. & Biophys.* 348(1):91-95.

Walsh, C.T. (1984). "Suicide substrates, mechanism-based enzyme inactivators: recent developments" *Ann. Rev. Biochem.* 53:493-535.

Washington, C.B. et al. (1995). "The Effect of N-Ethylmadeimide on the Na(+) -Dependent Nucleoside Transporter (N3) in Rabbit Choroid Plexus," *American Society for Pharmacology and Experimental Therapeutics* 274(1):110-114.

Wauquier, A. and Dugovic, C. (1990). "Serotonin and sleep-wakefulness" *Ann. N.Y. Acad. Sci.* 600:447-459.

Weil-Malherbe, H. (1978). "Serotonin and schizophrenia" Chapter 6 in *Serotonin in Health and Disease: vol. III: The Central Nervous System*. Essman, Walter B. ed., Spectrum Publications Inc: New York, pp. 231-291.

Wiley, J.S. et al. (1987). "Cytosine arabinoside in the treatment of T-cell acute lymphoblastic leukemia" *Aust. N.Z. J. Med.* 17:379-386.

Wiley, J.S. et al. (1989). "Nucleoside transport in acute leukaemia and lymphoma: close relation to proliferative rate" *Brit. J. Haematol.* 71:203-207.

Wouters, Walter et al. (1984). "Photoaffinity labeling of human brain dopamine receptors" *Biochem. Pharm.* 33(21):3517-3520.

Wouters, Walter et al. (1985). "Photoaffinity labelling of serotonin-$_2$ receptors with 7-azidoketanserin" *Eur. J. Pharm.* 107:399-400.

Young, J.D. et al. (1982). "Photoaffinity Labeling of the Human Erythrocyte Nucleoside Transporter by N6-(p-Azidobenzyl)adenosine and Nitrobenzylthioinosine. Evidence That the Transporter is a Band 4.5 Polypeptide," *The Journal of Biological Chemistry* 258(4):2202-2208.

* cited by examiner

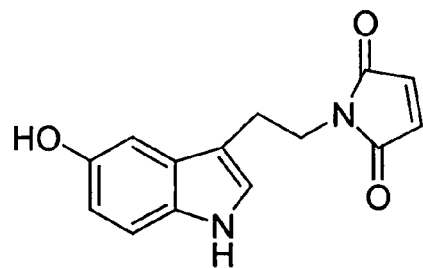
Figure 19a. LBT3001 (1-[2-(5-hydroxy-1*H*-indol-3-yl)-ethyl]-pyrrole-2,5-dione)
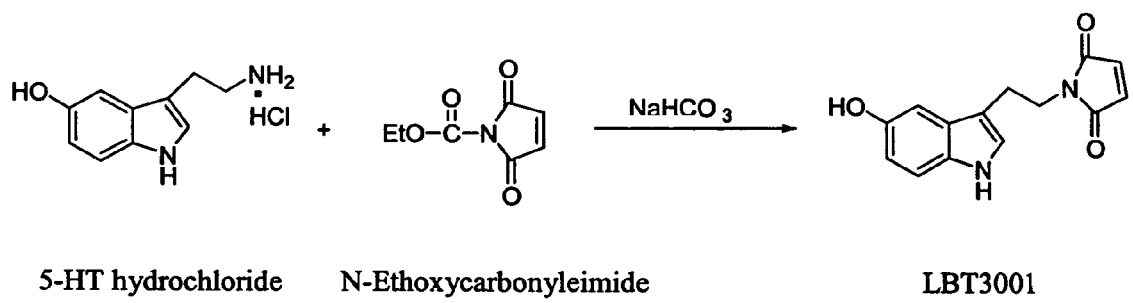
5-HT hydrochloride    N-Ethoxycarbonyleimide            LBT3001
Figure 19b. Reaction scheme for synthesis of LBT3001

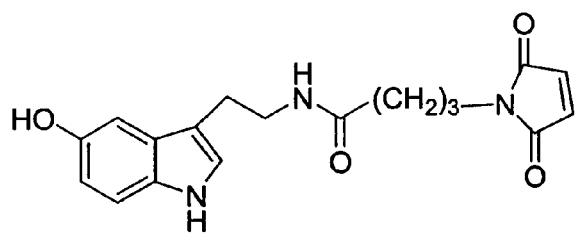
Figure 20a. LBT3002 (4-(2,5-dioxo-2,5-dihydro-pyrrol-1-yl)-N-[2-(5-hydroxy-1*H*-indol-3-yl)-ethyl]-butyramide)
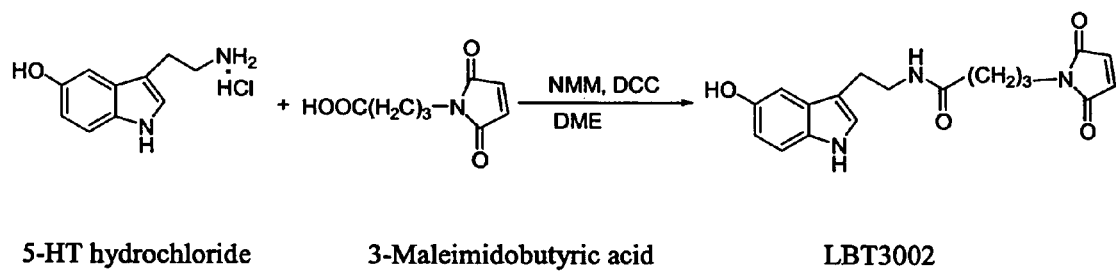
5-HT hydrochloride    3-Maleimidobutyric acid    LBT3002
Figure 20b. Reaction scheme for synthesis of LBT3002

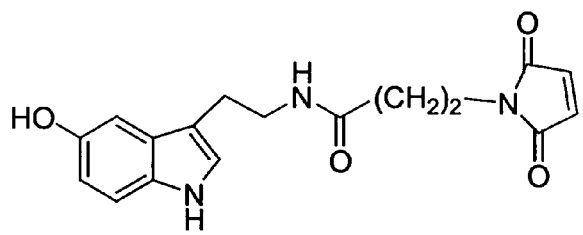
Figure 21a. LBT3004 (3-(2,5-dioxo-2,5-dihydro-pyrrol-1-yl)-N-[2-(5-hydroxy-1*H*-indol-3-yl)-ethyl]-propionamide)
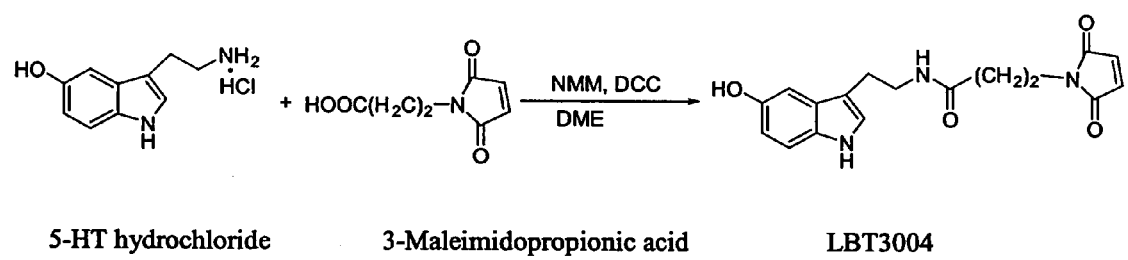
5-HT hydrochloride     3-Maleimidopropionic acid     LBT3004
Figure 21b. Reaction scheme for synthesis of LBT3004

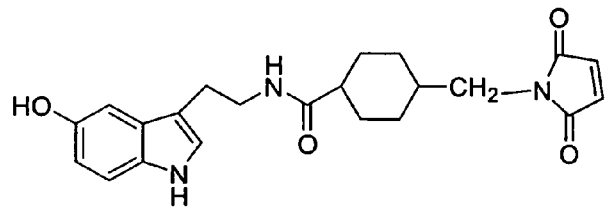
Figure 22a. LBT3005 (4-(2,5-dioxo-2,5-dihydro-pyrrol-1-ylmethyl)-cyclohexane carboxylic acid [2-(5-hydroxy-1H-indol-3-yl)-ethyl]-amide)
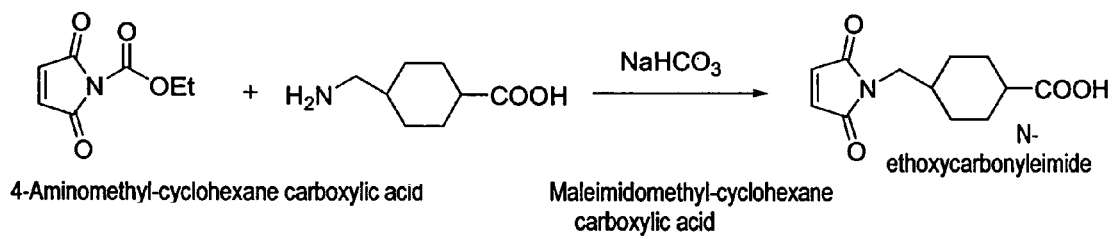
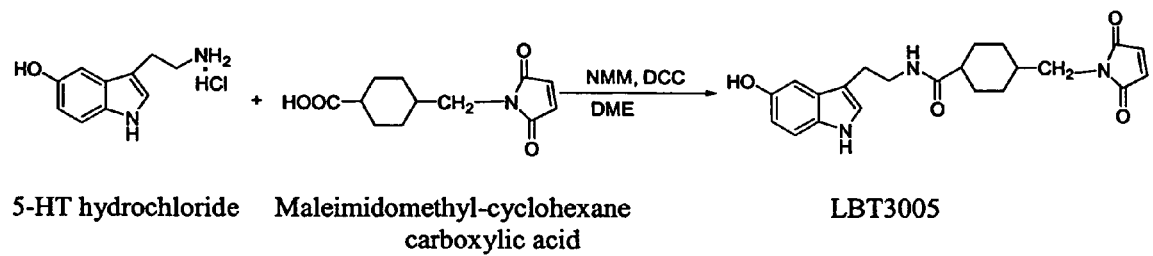
Figure 22b. Reaction scheme for synthesis of LBT3005

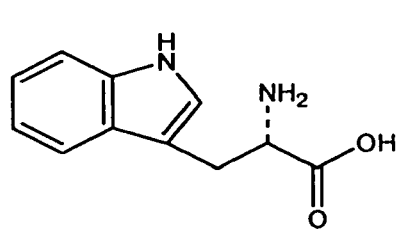
Tryptophan
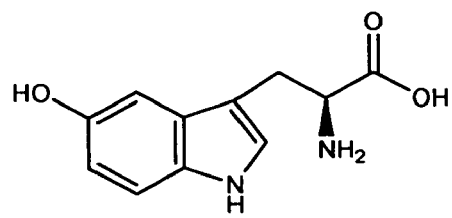
5-Hydroxytryptophan
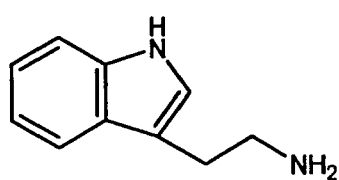
Tryptamine
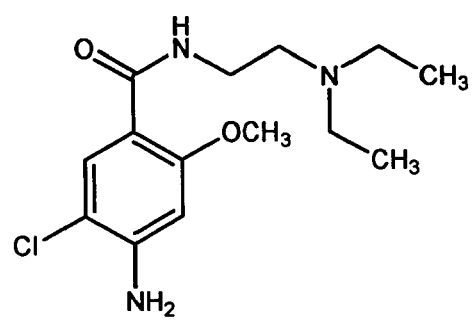
Metoclopramide
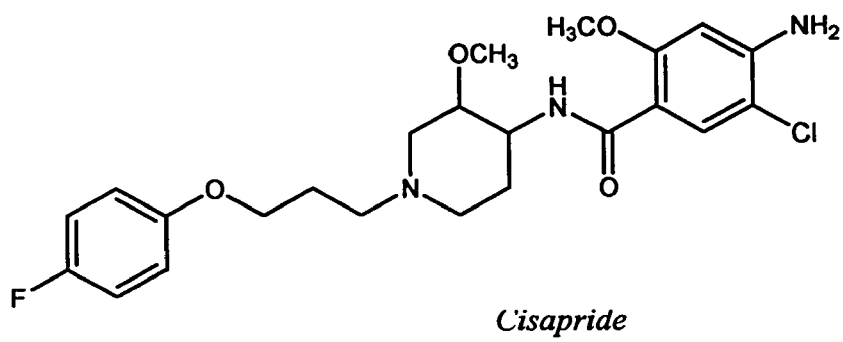
Cisapride
Figure 23

LIGANDS AND METHODS FOR PREPARING SAME

CROSS-REFERENCE TO RELATED APPLICATIONS

This application is a divisional of U.S. patent application Ser. No. 09/770,849 filed Jan. 26, 2001 now abandoned, which claims priority to U.S. Provisional Patent Application Ser. No. 60/178,756, filed Jan. 28, 2000, the disclosure of which is incorporated herein by reference in its entirety.

TECHNICAL FIELD

This invention relates generally to ligand-receptor interactions. In particular, the present invention relates to modified ligands that bind irreversibly to their cognate receptors, and to methods for preparing such ligands. The novel ligands of the invention have utility inter alia for investigating protein function and as drugs (in healthcare, agricultural and environmental applications) for more effectively inhibiting or stimulating cognate receptor function.

BACKGROUND ART

Pharmacological receptors are intracellular or membrane-bound proteins which produce a pharmacological effect after binding with a specific ligand. In this regard, a pharmacological receptor has a dual function to (a) detect a ligand signal by forming a ligand-receptor complex and to (b) conduct and translate the signal leading to the pharmacological effect.

Drugs can replace endogenous physiological ligands to interact with receptors. A prerequisite for such a drug-receptor interaction is the formation of a drug-receptor complex, just as in the case of ligand-receptor interaction. In contrast to physiological ligands that stimulate an effect after binding to a receptor (receptor-mediated effects), drugs can be classified as (a) agonists or drugs which stimulate an effect after binding to the receptor, and (b) antagonists or drugs which do not stimulate an effect after receptor binding.

Several types of molecular interactions are possible for drug-receptor binding including ionic bonds, hydrogen bonds, and hydrophobic bonds by van der Waals forces. The vast majority of receptor interactions involve several kinds of binding simultaneously. Ionic bonds are important for the primary phase of drug-receptor interaction since these bonds have the greatest or longest range. After the initial interaction, fine-tuning takes place involving dipole-dipole-bonds, hydrogen bonds and hydrophobic bonds. Although all these interactions also fix the drug molecule in the receptor's active site, the bindings are nevertheless reversible, as the force of interaction is very weak. Hence the pharmacological effectiveness of any drug is often affected by its own concentration in the plasma, as a decrease in plasma drug concentration will increase the dissociation of drug molecule from its receptor.

Several agents are known to inhibit enzymes irreversibly or pseudoirreversibly and the precise mechanism of inhibition gives rise to subtle differences in the inhibition profiles and the duration of inhibition.

Many inhibitors of acetylcholinesterase react covalently with this enzyme to form an acyl enzyme that deacylates more slowly than the acetyl enzyme formed with the natural substrate acetylcholine. The acetyl enzyme forms rapidly by attack of the active site serine on the substrate. Transfer of the acyl group to the enzyme occurs through a tetrahedral intermediate. The acetyl enzyme is rapidly hydrolyzed, with a halftime of 10 μsec. These rapid acylation and deacylation steps give rise to a turnover rate of $10^5$ substrate molecules per enzyme molecule per second. Cholinesterase inhibitors such as physostigmine and neostigmine form methylaminocarbamyol and dimethylaminocarbamoyl enzymes, which have half times for deacylation of several minutes. Thus, by providing the enzyme with an alternative substrate, catalysis of acetylcholine is precluded during the catalytic cycle for the carbamoylating agent. The kinetic constants for the respective acylation steps for the acetoxy and carbamoxy ester substrates do not greatly differ; hence the longer residence time of the carbamoyl enzyme conjugate is an important factor in favoring inhibition.

Several other enzymes are inhibited by covalent attachment of the inhibitor, giving rise to irreversibility. The hydrazines (phenelzine, isocarxazid metabolites) and the acetylenic agents (pargyline) are oxidized to reactive intermediates by monoamine oxidase. These intermediates attack the associated flavin cofactor on the enzyme. Such agents have been termed suicide substrates since their activation requires catalysis by the very enzyme that they inactivate. Hence the inactivation process is mechanism-based. There are now many examples of such substrates, activation of which by the enzyme results in covalent modification of the enzyme or of an associated cofactor. Often this occurs by conjugation or association of the enzyme with its substrate followed by a neighboring group attack. Several of the targets of suicide substrates have therapeutic significance. These include the penicillinases and alanine racemases in antibacterial design; GABA transaminase inhibitors for anti-epileptic agents; lipoxygenase and cyclooxygenase inhibitors to control leukotriene and prostaglandin biosynthesis, respectively, aromatase inhibitors to block formation of estrogenic hormones; ornithine decarboxylase inhibitors as antiparasitic agents; and dopamine β-hydroxylase inhibitors to control catecholamine biosynthesis. Many suicide substrates serve as antimetabolites and are potential antineoplastic agents. The effectiveness of these inhibitors depends not only on their relative dissociation constants or $K_m$ values compared with those of the endogenous substrate but also on kinetic competition between turnover of the suicide substrate and the inactivation event.

Omeprazole (PRILOSEC) is another well-known irreversible binding drug that has been released for clinical use. This drug inhibits gastric acid secretion by binding to the $H^+$, $K^+$-ATPase present only in the apical membrane of parietal cells. Omeprazole is especially useful in patients with hypergastrinemia and may be valuable in those whose peptic ulcer disease is not well controlled by $H_2$ antagonists. Omeprazole contains a sulfinyl group in a bridge between substituted benzimidazole and pyridine rings. At neutral pH, this drug is a chemically stable, lipid-soluble, weak base that is devoid of inhibitory activity. This neutral weak base reaches parietal cells from the blood and diffuses into the secretory canaliculi, where the drug becomes protonated and thereby trapped. Protonated drug rearranges to form a sulfenic acid and a sulfenamide. The sulfenamide interacts covalently with sulfhydryl group at critical sites in the extracellular (luminal) domain of the membrane-spanning $H^+$, $K^+$-ATPase. Omeprazole must thus be considered as prodrug that needs to be activated to be effective.

Despite the availability of several agents that bind their targets irreversibly, there is a dearth of methods currently available for rationally designing ligands to irreversibly bind a target receptor.

DISCLOSURE OF THE INVENTION

The present invention arises, at least in part, from the unexpected discovery that by attaching a conjugation agent to a parent ligand that reversibly binds a target receptor, wherein the conjugation agent is reactive with a moiety of the target receptor such that a covalent bond is formable between the conjugation agent and the moiety, the modified ligand thus produced is capable of binding the target receptor irreversibly.

Accordingly, in one aspect of the invention, there is provided a process for modifying a parent ligand, comprising attaching to said parent ligand a conjugation agent that is reactive with a moiety of a target receptor to which said parent ligand binds such that a covalent bond is formable between said conjugation agent and said moiety.

Suitably, the conjugation agent is attached to the parent ligand through a spacer.

Preferably, the spacer is covalently attached to the parent ligand.

Preferably, the spacer is covalently attached to the conjugation agent.

The spacer is suitably radical selected from the group consisting of alkyl, heteroalkyl, cycloalkyl, heterocycloalkyl, oxoalkyl, heterooxoalkyl, alkenyl, hetero alkenyl, aralkyl, hetero aralkyl, aryl and heteroaryl radicals or any other molecular conformation which serves the function of being a spacer. The length of the spacer arm is suitably selected from a range of between about 0 Å and about 20 Å.

Preferably, the spacer is a non-hydrolysable radical under physiological conditions.

Preferably, the conjugation agent is selected from the group consisting of a sulfhydryl group specific conjugation agent, an amino group specific conjugation agent, a carboxyl group specific conjugation agent, a tyrosine specific conjugation agent, an arginine specific conjugation agent, a histidine specific conjugation agent, a methionine specific conjugation agent, a tryptophan specific conjugation agent, and a serine specific conjugation agent.

The sulfhydryl group specific conjugation agent may be selected from the group consisting of N-maleimide, N-maleimide derivatives and disulfide reagents including, but not restricted to, 5'-dithiobis-2-nitrobenzoic acid), 4,4'-dithiodipyridine, methyl-3-nitro-2-pyridyl disulfide, and methyl-2-pyridyl disulfide.

The amino group specific conjugation agent may be selected from the group consisting of alkylating agents including, but not restricted to, α-haloacetyl compounds, aryl halides, aldehydes and ketones, and acylating agents including, but not restricted to, isocyanate, isothiocyanate, imidoesters, N-hydroxylsuccinimidyl ester, ρ-nitrophenyl ester, acyl chloride, and sulfonyl chloride.

The carboxyl group specific conjugation agent may be selected from the group consisting of carbodiimides and carboxyl group esterification reagents including, but not restricted to, diazoacetate esters and diazoacetamides.

The tyrosine specific conjugation agent may be selected from diazonium derivatives including, but not limited to, benzidine and bis-diazotized 3,3'-dimethylbenzidine.

The arginine specific conjugation agent may be selected from 1,2-dicarbonyl reagents including, but not restricted to, glyoxal, phenylglyoxal, 2-3-butanedione and 1,2-cyclohexanedione.

The histidine specific conjugation agent is suitably selected from the group consisting of alkylating agents including, but not restricted to, α-haloacetyl compounds, aryl halides, aldehydes and ketones, and acylating agents including, but not restricted to, diethylpyrocarbonate, ethoxyformic anhydride, isocyanate, isothiocyanate, imidoesters, N-hydroyxlsuccinimidyl ester, ρ-nitrophenyl ester, acyl chloride, and sulfonyl chloride.

The methionine specific conjugation agent may be selected from the group consisting of alkylating agents including, but not restricted to, α-haloacetyl compounds, aryl halides, aldehydes and ketones.

The tryptophan specific conjugation agent may be selected from the group consisting of N-bromosuccinimide, 2-hydroxy-5-nitrobenzyl bromide and ρ-nitrophenylsulfenyl chloride.

The serine specific conjugation agent may be selected from the group consisting of diisopropylfluorophosphate and acrylsulfonyl fluorides including, but not restricted to, phenylmethyl-sulfonylfluoride.

The parent ligand may be any natural or non-natural ligand but is preferably a biologically active ligand inclusive of known drugs and naturally occurring or synthesized drug candidate compounds.

In another aspect, the invention provides a modified ligand produced by the process broadly described above.

In yet another aspect of the invention, there is provided a modified ligand having the general formula:

$$L-R_1-A \qquad (I)$$

wherein L is a parent ligand;

wherein A is a conjugation agent that is reactive with a moiety of a target receptor to which the parent ligand binds such that a covalent bond is formable between said conjugation agent and said moiety; and $R_1$ is an optional spacer which preferably comprises a non-hydrolysable radical selected from the group consisting of alkyl, heteroalkyl, cycloalkyl, heterocycloalkyl, oxoalkyl, heterooxoalkyl, alkenyl, hetero alkenyl, aralkyl, hetero aralkyl, aryl and heteroaryl radicals.

In a preferred embodiment, the modified ligand is interactive with es nucleoside transporter and/or nucleoside/nucleotide/nucleobase-sensitive proteins, wherein said modified ligand has a general formula selected from the group consisting of:

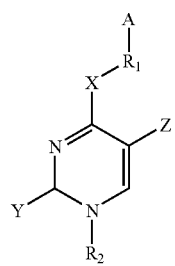

(II)

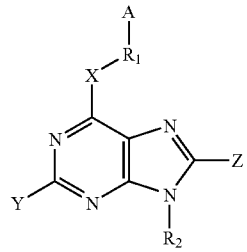

(III)

wherein A is N-maleimide, 2-pyridyldithio, or halogen; X is NH, S, or O; Y is H, halogen, $NH_2$, or O; Z is H, halogen, or $CH_3$; $R_1$ is spacer arm comprising a non-hydrolysable radical preferably under physiological conditions; $R_2$ is H, β-D-ribose, β-D-2-deoxyribose, or their 5'-mono-, 5' di-, and 5' tri-phosphate.

Suitably, the modified ligand inhibits said es nucleoside transporter and/or nucleoside/nucleotide/nucleobase-sensitive proteins and has a general formula selected from the group consisting of:

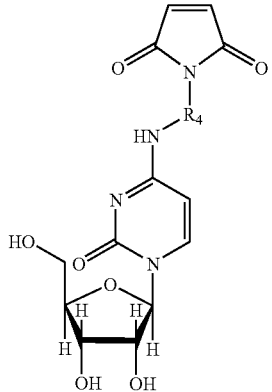

(IV)

wherein $R_4$ is 4-[N-methyl]cyclohexane carboxylate, N-[m-benzoate], 4-[p-phenyl]butyrate, N-[γ-butyrate], N-[α-acetate], or N-[ε-caproylate];

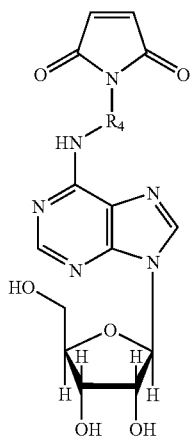

(V)

wherein $R_4$ is 4-[N-methyl]cyclohexane carboxylate, N-[m-benzoate], 4-[p-phenyl]butyrate, N-[γ-butyrate], N-[α-acetate], or N-[ε-caproylate];

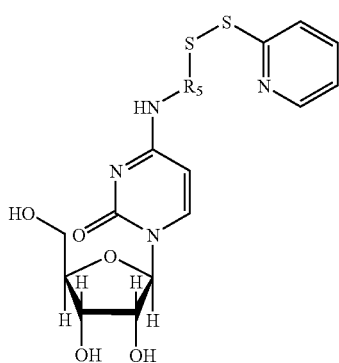

(VI)

wherein $R_5$ is 4-carbonyl-α-methyl-α-toluene, 6-[α-methyl-α-tuloamido]-hexanoate, N-[3-propionate], or 6-[3'-propioamido]hexanoate; and

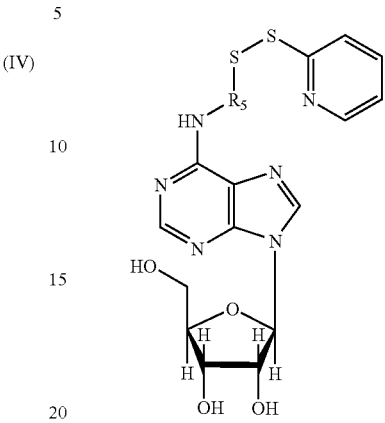

wherein $R_5$ is 4-carbonyl-α-methyl-α-toluene, 6-[α-methyl-α-tuloamido]-hexanoate, N-[3-propionate], or 6-[3'-propioamido]hexanoate.

In another embodiment modified ligands that bind to seratonin receptors can be used.

In another aspect, the invention resides in a composition comprising the modified ligand as broadly described above, together with a pharmaceutically acceptable carrier.

In a further aspect of the invention, there is provided a method of treatment or prophylaxis of a condition associated with a target receptor, said method comprising administering to a patient in need of such treatment a therapeutically effective dosage of the composition as broadly described above.

According to another aspect of the invention, there is provided a method of detecting the presence of a target receptor in a test sample, comprising: contacting said sample with a modified ligand as broadly described above, wherein said modified ligand binds said target receptor; and detecting the presence of a complex comprising said modified ligand and said receptor in said contacted sample.

In another aspect of the invention, there is provided a method of quantifying the presence of a target receptor in a test sample, comprising: contacting said sample with a modified ligand as broadly described above, wherein said modified ligand binds said target receptor; measuring the concentration of a complex comprising said modified ligand and said receptor in said contacted sample; and relating said measured complex concentration to the concentration of said receptor in said sample.

In yet another aspect, the invention provides a method of detecting the presence of a target receptor on a cell or cell membrane, comprising: contacting a sample containing said cell or cell membrane with a modified ligand as broadly described above, wherein said modified ligand binds said target receptor; and detecting the presence of a complex comprising said modified ligand and said cell or cell membrane in said contacted sample.

In another aspect of the invention, there is provided a method of quantifying the presence of a target receptor on a cell or cell membrane, comprising: contacting a sample containing said cell or cell membrane with a modified ligand as broadly described above, wherein said modified ligand binds said target receptor; measuring the concentration of a complex comprising said modified ligand and said cell or cell membrane in said contacted sample; and relating said measured complex concentration to the concentration of said receptor present on said cell or cell membrane.

In another aspect, the invention extends to a probe that covalently binds to a target receptor, said probe comprising a modified ligand as broadly described above having a reporter molecule associated therewith.

In one embodiment, the probe comprises the modified ligand that is interactive with es nucleoside transporter and/or nucleoside/nucleotide/nucleobase-sensitive proteins, as broadly described above.

In this respect, the cell is preferably an animal cell, more preferably a mammalian cell, and more preferably a human cell. Alternatively, the cell may be a plant cell or a microbial cell. The microbial cell includes, but is not restricted to, a cell of bacterial, viral or fungal origin.

The invention also encompasses the use of the modified ligand and probe as broadly described above inter alia in the study, treatment and prevention of conditions associated with their corresponding target receptors.

In one embodiment, there is provided process for modifying a parent ligand, comprising attaching to said parent ligand a conjugation agent that is reactive with a moiety of a target receptor to which said parent ligand binds, wherein when said parent ligand binds to the receptor a covalent bond is formed between said conjugation agent and said moiety.

In one preferred embodiment, the conjugation agent is positioned on the ligand at a position that promotes and/or permits covalent bond formation with the moiety of the target receptor. In another preferred embodiment, the receptor to which the ligand binds is an active site associated with a biological activity. The receptor is, for example, a cell surface receptor. The binding of the modified ligand to the receptor in one embodiment is associated with altered activity of the target receptor.

In another preferred embodiment, the parent ligand and/or receptor are naturally occurring. In another embodiment, the modified ligand is not a crosslinking agent. In another embodiment, the modified ligand optionally does not comprise a photo-reactive group such as a photolabel. In another embodiment, the modified ligand does not comprise a label. In another embodiment, the receptor to which the ligand binds is not a nucleic acid, such as RNA or DNA. In another embodiment, the conjugation agent does not bind to a moiety of a nucleic acid, and optionally binds to a residue of an amino acid.

In one embodiment, there is provided process for modifying a parent ligand, comprising attaching to said parent ligand a conjugation agent that is reactive with a moiety of a target receptor to which said parent ligand binds, wherein when said parent ligand binds to the receptor a covalent bond is formed between said conjugation agent and said moiety, and wherein the parent ligand binds specifically with a nucleoside transporter.

In another embodiment, there is provided a process for modifying a parent ligand, comprising attaching to said parent ligand a sulfhydryl group specific conjugation agent that is reactive with a sulfhydryl group of a target receptor to which said parent ligand binds, wherein when said parent ligand binds to the receptor a covalent bond is formed between said conjugation agent and said sulfhydryl group, and wherein the parent ligand binds specifically with a serotonin receptor.

In one embodiment, there is provided a modified ligand having the general formula:

$$L\text{-}R_1\text{-}A \quad (I)$$

wherein L is a parent ligand that binds specifically with a target receptor comprising a nucleoside transporter;

wherein A is a conjugation agent that is reactive with a moiety of the target receptor to which the parent ligand binds, such that when said parent ligand binds to the receptor a covalent bond is formed between said conjugation agent and said moiety; and $R_1$ is an optional spacer.

In another embodiment, there is provided a modified ligand having the general formula:

$$L\text{-}R_1\text{-}A \quad (I)$$

wherein L is a parent ligand that binds specifically with a target serotonin receptor;

wherein A is a conjugation agent that is reactive with a sulfhydryl group of said target receptor to which the parent ligand binds, such that when said parent ligand binds to the receptor a covalent bond is formed between said conjugation agent and said sulfhydryl group of said receptor; and $R_1$ is an optional spacer.

The disclosure of all patents, patent applications, publications and published patent applications referred to herein are incorporated herein by reference in their entirety.

BRIEF DESCRIPTION OF THE DRAWINGS

The invention, as exemplified by preferred embodiments, is described with reference to the following drawings in which:

FIG. 19a shows the chemical structure of LBT3001 (1-[2-(5-hydroxy-1H-indol-3-yl)-ethyl]-pyrrole-2,5-dione)).

FIG. 19b shows the reaction scheme for synthesis of LBT3001.

FIG. 20a shows the chemical structure of LBT3002 (4-(2,5-dioxo-2,5-dihydro-pyrrol-1-yl)-N-[2-(5-hydroxyl-1H-indol-3-yl)-ethyl]-butyramide).

FIG. 20b shows the reaction scheme for synthesis of LBT3002.

FIG. 21a shows chemical structure of LBT3004 (3-2,5-dioxo-2,5-dihydro-pyrrol-1-yl)-N-[2-(5-hydroxyl-1H-indol-3-yl)-ethyl]-propionamide).

FIG. 21b shows the reaction scheme for synthesis of LBT3004.

FIG. 22a shows the chemical structure of LBT3005 (4-(2,5-dioxo-2,5-dihydro-pyrrol-1-yl-methyl)-cyclohexane carboxylic acid [2-5-hydroxy-1H-indol-3-yl)-ethyl]-amide).

FIG. 22b shows the reaction scheme for synthesis of LBT3005.

FIG. 23 shows the structures of exemplary ligands that can be modified to include a conjugation agent.

DETAILED DESCRIPTION

1. Definitions

Figure 1:
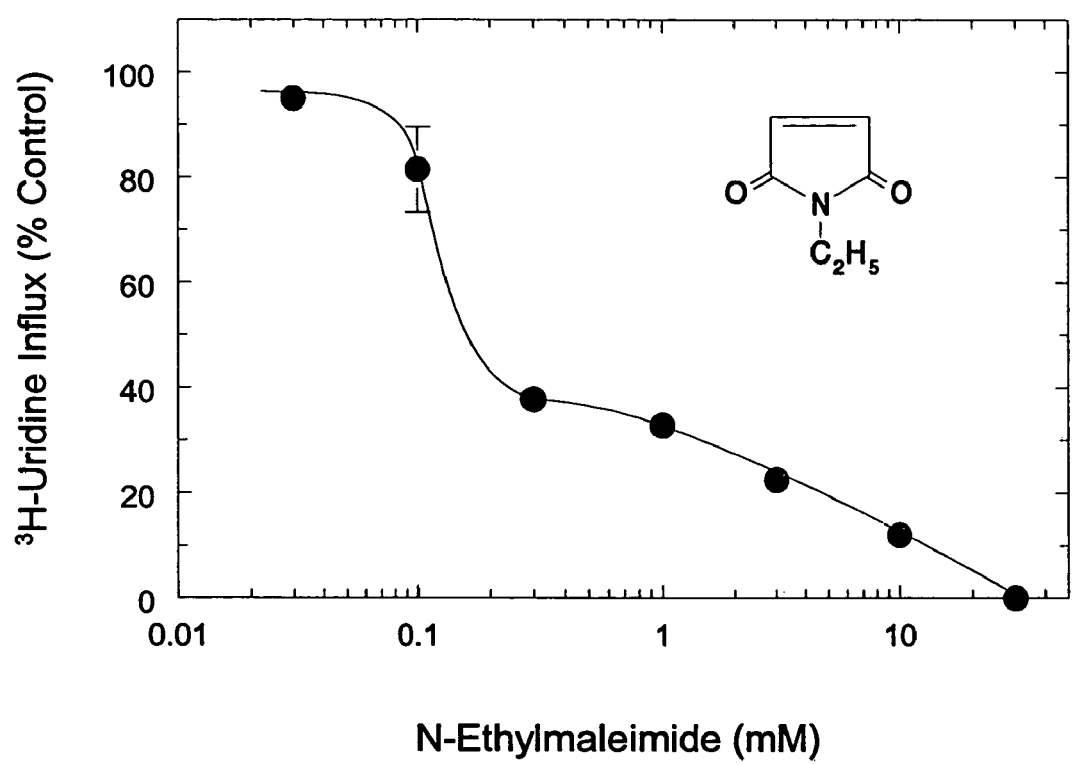
FIG. 1 shows the NEM inhibition of equilibrative $^3$H-uridine transport in murine myeloma SP2/0-Ag14 cells.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "attached" is meant direct or indirect attachment of a conjugation agent to a ligand in such a manner as to resist separation of the conjugation agent from the ligand under normal physiological conditions. Accordingly, the term "attached" as used herein includes within its scope one more ionic bonds, hydrogen bonds, van der Waals forces, covalent bonds or combinations thereof that form between the conjugation agent and the ligand or between an intervening spacer and the conjugation agent and the ligand, respectively, such that separation of the conjugation agent from the ligand is resisted under normal physiological conditions.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "conjugation agent" is meant a moiety of a modified ligand that is reactive with a moiety of a receptor that binds a parent ligand from which the modified ligand was derived wherein a covalent bond is formable between the conjugation agent and the receptor moiety. In this connection, the conjugation agent may be sufficient either on its own or in the presence of an ancillary conjugation agent to facilitate covalent coupling with the receptor moiety. The ancillary coupling agent may be an enzyme that catalyzes, or an activating agent that causes, formation of a covalent bond between the conjugation agent and said receptor moiety.

By "isolated" is meant material that is substantially or essentially free from components that normally accompany it in its native state.

As used herein, the term "ligand" refers to an agent that binds, interacts or otherwise associates with, a target receptor. The agent may bind the target receptor when the target receptor is in its native conformation, or when it is partially or totally unfolded or denatured. According to the present invention, a ligand is not limited to an agent that binds a recognized functional region of the target receptor e.g. the hormone-binding site of a receptor, and the like. In practicing the present invention, a ligand can also be an agent that binds any surface or internal sequences or conformational domains of the target receptor. Preferably, the ligand is a molecule affecting physiological function including a drug. The ligand can also be an endogenous ligand.

By "obtained from" is meant that a sample such as, for example, an extract comprising a receptor is isolated from, or derived from, a particular source such as a suitable cell or tissue source inclusive of human, animal, plant or microbial origin.

The term "patient" as used herein refers to any organism in which therapy or prophylaxis of a condition associated with a receptor is desired using the methods of the invention. However, it will be understood that "patient" does not imply that symptoms are present. The patient may therefore include a microbe, plant or animal. Preferably, the patient is a human or other mammal and includes any individual it is desired to examine or treat using the methods of the invention. Suitable mammals that fall within the scope of the invention include, but are not restricted to, primates, livestock animals (e.g., sheep, cows, horses, donkeys, pigs), laboratory test animals (e.g., rabbits, mice, rats, guinea pigs, hamsters), companion animals (e.g. cats, dogs) and captive wild animals (e.g., foxes, deer, dingoes).

By "pharmaceutically acceptable carrier" is meant a solid or liquid filler, diluent or encapsulating substance that may be safely used in topical or systemic administration.

The term "pharmaceutically acceptable salts" as used herein refers to non-toxic salts of the modified ligands of this invention, which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

The term "receptor" as used herein refers to a structure including a molecule or a cluster of molecules that is specific for one or more ligands wherein binding, interaction or otherwise association of the ligand(s) with the receptor effects, changes or nullifies a function of the receptor. The receptor is preferably, but not exclusively, a protein. Representative receptors include, but are not limited to, an insulin receptor, epidermal growth factor receptors, γ-aminobutyric acid receptors, nicotinic acetylcholine receptors, serotonin receptors, α- and β-adrenoceptors, dopamine receptors, histamine receptors, prostanoid receptors, adenosine receptors, cyclic nucleotide receptors, glutamate receptors, cytokine receptors, atrial naturetic peptide receptors, and the prostaglandin receptors. The receptor can include transporters such as glucose, amino acids transporters, sodium-proton exchangers, chloride-bicarbonate exchangers, sodium pumps, calcium pumps, proton pumps; channels such as sodium channels, potassium channels, calcium channels and chloride channels; enzymes such as oxidoreductases, transferases, hydrolases, lyases, isomerases, and ligases. However, it will be understood that the receptor need not be a protein and may include, for example, a nucleic acid in which the amino group found on adenine, guanine and cytosine may be targeted by a conjugation agent according to the invention. Alternatively, the receptor may be a carbohydrate (e.g., amino-containing carbohydrates such as aminophenyl glycosides) or a lipid (e.g., present on the phosphate head groups of some phospholipids) having one or more carboxyl groups, and/or one or more amino groups that may be targeted by a conjugation agent.

By "reporter molecule" as used in the present specification is meant a molecule that, by its chemical nature, provides an analytically identifiable signal that allows the detection of a complex comprising a ligand and its cognate receptor. The term "reporter molecule" also extends to use of cell agglutination or inhibition of agglutination such as red blood cells on latex beads, and the like.

The term "sample" as used herein refers to any suitable sample that may contain a target receptor according to the invention. The sample may be extracted, untreated, treated, diluted or concentrated from any suitable source and may contain one or more cells and/or cell membranes. The sample may comprise whole cells, denatured cells, cellular membranes or parts thereof. Alternatively, the sample may contain an isolated receptor. Suitably, the sample may comprise cells obtained from a tissue biopsy. Alternatively, the sample may comprise cells or cell lines, which have been cultured in vitro.

The term "spacer" as used herein refers to a chemical linker, polymer, peptide and the like that spatially separates the conjugation agent from the ligand. Preferably, the spacer is selected such that it does not interfere with the binding of the modified ligand to the receptor.

By "therapeutically effective amount", in the context of the treatment of a condition associated with a receptor, is meant the administration of that amount to a patient in need of such treatment, either in a single dose or as part of a series, that is effective for treatment of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

2. Modified Ligands

The present invention resides, at least in part, in the surprising discovery that a conjugation agent can be attached to a parent ligand to form a modified ligand that binds irreversibly to a target receptor to which the parent ligand binds reversibly. The irreversible binding of the modified ligand to the receptor is effected by formation of a covalent bond between the conjugation agent and a moiety present on the receptor, which is preferably one or more functional amino acid side chain groups (sometimes referred to herein as "functional groups"). The covalent bond is formed by association of the modified ligand with the receptor, followed by neighboring reactive functional group attack by the conjugation agent. This irreversible interaction of the modified ligand with the receptor results in either permanent inhibition (for an antagonist) or stimulation (for an agonist) of the receptor functions. Normal function or activity of the receptor resumes only after new receptors are synthesized.

Parent ligands that can be modified include ligands that are interactive with es nucleoside transporter and/or nucleoside/nucleotide/nucleobase-sensitive proteins. Two forms of nucleoside trasporters are classified based on their sensitivity to inhibition by NBMPR (nitrobenzylthioinosine). See Griffith et al., *Biochim. Biophys. Acta*, vol. 1286, pp. 153–181 (1996). The group of transporters sensitive to NBMPR is designated es (equilibrium sensitive), and the group insensitive is designated ei (equilibrium insensitive). In one embodiment, compounds are provided that have differential binding to es vs. ei receptors. Compounds are provided that bind selectively and irreversibly to es receptors. The expression of es receptors is positively correlated with the carcinogenic state of cells.

Among the numerous reactive functional amino acid side chains on the es nucleoside transporter proteins that can be used for covalent attachment, the sulfhydryl group of cysteine residue is probably the most pharmacological and biologically important. Early studies on the effect of sulfhydryl reagents on nucleoside transport in mammalian cells had shown to cause a marked inhibition of uridine uptake in a variety of cultured cells. (Plagemann & Richey (1974), *Biochim. Biophs. Acta*, vol. 344, pp. 263–305; Plagemann et al. (1978), *J. Cell. Physiol.*, vol. 97, pp. 49–72; Plagemann & Wohlhueter (1980), *Curr. Top. Membr. Transp.*, vol. 14, pp. 225–230; Belt (1983), *Biochem. Biophys. Res. Commun.*, vol. 110, pp. 417–423; Belt (1983), *Mol. Pharmacol.*, vol. 24, pp. 479–484). However most of the earlier studies were directed toward the total nucleoside uptake and little attempt were made to distinguish the differential in sensitivity towards sulfhydryl reagents by the es and ei transport systems. Furthermore, the sulfhydryl reagents used were mainly of organomercurial compounds, which were demonstrated to perturb plasma structure at concentration as low as 200 μM (Belt & Noel (1985), *Biochem. J.*, vol. 232, pp.681–688).

Ligands also may be modified which are ligands that bind to serotonin (5-hydroxytryptamine, or 5-HT) receptors. 5-HT receptors include a diversity of receptor subtypes (Peroutka, S. J., *CNS Drugs*, (1995), vol. 4 (Suppl 1), pp. 18–28). With the exception of the 5-HT$_3$ receptor, which is an ion channel (Derkash, V. et. al., *Nature*, (1989), vol. 339, pp. 706–709), other 5-HT receptors belong to the extensive family of seven transmembrane G protein-coupled receptors. The clinical significance of the effects of 5-HT is manifest for example, in neurological, CNS, psychiatric and mood disorders, including migraine, anxiety, depression, schizophrenia, obsessive compulsive disorder, psychosis, aggression, hostility, eating disorders, gastrointestinal disorders, hypertension, the maintenance of the circadian rhythms in the sleep-wakefulness cycle, sexual activity, compulsive behavior, temperature, emesis, and cardiovascular and motor function. Drugs that target the 5-HT receptors thus have wide clinical applications. Ligands that bind to 5-HT receptors can have effects by binding, for example, to the cardiovascular system, platelets, gastrointestinal tract, and the brain (Erspamer, V, Ed. "5-Hydroxytryptamine and Related Indolealklylamines", *Handbuch der Expermentellen Pharmakologie*, Vol. 19. Springer-Verlag, Berlin, (1996), pp. 132–181).

Thus, for example, the ligand 5-HT may be modified as disclosed herein. Other ligands that can be modified include 5-HT precursors and 5-HT receptor agonists and antagonists known in the art. Examples include the precursor 5-hydroxytyptophan, which has been used as an antidepressant drug; 5-$HT_{1A}$-agonists used as tranquilizers and antihypertensives; sumatriptan, a selective 5-$HT_1$ receptor agonist; used for migraine; 5-$HT_2$-antagonists such as methysergide, used for migraine prophylaxis and in carcinoid tumour syndrome; 5-$HT_2$-antagonists such as ketaserin, used to lower the blood pressure in hypertensive patients; and selective 5-$HT_3$-antagonists used to treat cytostatic- and radiation-induced emesis. (Beasley, C. M., et. al., *Psychopharmacology*, (1992), vol. 107, pp. 1–10; Bolden-Watson, C., and Richelson, E., *Life Sciences*, (1993), vol. 52, pp. 1023–1029; Koe, B. K., *J. Clin. Psychiatry*, (1990), vol. 51, pp. 13–17).

Serotonin binding ligands which can be modifed include those developed for CNS disorders, such as anxiety, such as benzodiazepines, or 5-$HT_{1A}$ agonists, such as buspirone, gepirone, ipsapirone, and flesinoxan. As anxiolytic agents, they possess advantages over benzodiazepines because they lack the sedation and drug dependence liabilities of bezodiazepines (Barrett, J. E., and Vanover, K. E., *Psychopharmacology*, (1993), vol. 112, pp. 1–12.). Other serotonin binding ligands include those developed for treatment of depression, such as SSR15, for example fluoxetine. SSR15 have also been shown to have efficacy in the treatment of bulimia and obsessive-compulsive disorders and may be also useful in treating obesity, panic disorders, premenstrual syndrome, diabetic neuropathy, chronic pain, and certain cognitive aspects of Alzheimer's disease. Other useful antidepressant drugs which are relatively potent antagonists at 5-$HT_2$ receptors, include tricyclic antidepressants, such as trazadone and nefazodone (Cowen, P. J., and Anderson. L. M., "5-Hydroxytryptamine in Psychiatry" (Sandler, M., Coppen, A., & Harnett, S. Eds), Oxford University Press, New York, (1991)). Ligands include compounds developed for the treatment of schizoprenia, including the antipsychotic agents clozapine, risperidone, and olanzepine, (Weil-Malherbe, H., Serotonin and schizophrenia. In "*The Central Nervous System. Vol. 3, Serotonin in Health and Disease*", Essman, W. B., Ed, Spectrum Publications, Inc., New York, (1978), pp. 231–291). Ligands associated with the treatment of eating disorders can be used, such as the SSR15 and fenfluramine. Fenfluramine may be useful in the treatment of other diseases, such as autism, premenstrual syndrome, seasonal affective disorder, and attention deficit disorder. Ligands associated with alleviation of gastrointestinal disorders can be used, such as ondansetron and granisetron, which are used in the treatment of radiation induced emesis associated with cancer chemotherapy, and for ameliorating the nausea and vomiting occurring during recovery from general anesthesia Other ligands include metoclopramide and cisapride. Ligands used in control of the sleep-wakefulness cycle, such as L-tryptophan or nonselective 5-HT agonists or 5-HT antagonists such as ritanserin may be used (for a review, see Wauquier, A., and Dugovic, C., *Ann N.Y. Acad. Sci.*, (1990), vol. 600, pp. 447–459). Other ligands include etanserin, a 5-$HT_2$ receptor antagonist used as an antihypertensive agent.

2.1. Considerations Relating to Protein Structure Reactivity

Peptides and proteins are composed of amino acids polymerized together through the formation of peptide (amide) bonds. The peptide-bonded polymer forms the backbone of polypeptide structure. There are 20 common amino acids found throughout nature, each containing an identifying side chain of particular chemical structure, charge, hydrogen bonding capability, hydrophilicity (or hydrophobicity), and reactivity. The side chains do not participate in peptide formation and are thus free to interact and react with their environment.

Amino acids may be grouped by type depending on the characteristics of their side chains. The most significant amino acids for covalent conjugation purposes are the ones containing accessible ionizable side chains such as aspartic acid, glutamic acid, lysine, arginine, histidine, cysteine, and tyrosine. Methionine and tryptophan also containing ionizable side chains, however, they are not easily accessible as they are usually buried deep inside the molecular structure of receptors due to their hydrophobic nature.

Both aspartic and glutamic acids contain carboxylate groups that have ionization properties. Carboxylate groups in proteins may be derivatized through the use of amide bond forming agents or through active ester or reactive carbonyl intermediates.

Lysine, arginine, and histidine have ionizable amine containing side chains. These amine containing side chains typically are exposed on the surface of proteins and can be derivatized with ease. The most important reactions that can occur with these residues are alkylation and acylation.

Cysteine is the only amino acid containing a sulffiydryl group. The most important reaction of cysteine groups in proteins is the formation of disulfide cross-links with another cysteine molecule. Cysteine sulfhydryls and cystine disulfides (called cystine residues) may undergo a variety of reactions, including alkylation to form stable thioether derivatives, acylation to form relatively unstable thioesters, and a number of oxidation and reduction processes. Cysteine and cystine groups are relatively hydrophobic and usually found within the core of a protein. It is often difficult to access the sulfhydryl groups of large proteins without the presence of a deforming agent or a "driver". Nevertheless, such steric hindrance does give the sulfhydryl groups a leading edge in selectivity. Thus, to access the functional reactive sulffiydryl group situated deep into the ligand-binding site, without using deforming agents, is to utilize its physiological ligands or drugs to direct the conjugation agent as herein described into the inner structure of receptors. It is possible that irreversible binding drugs that are targeted at the sulfhydryl groups is likely to have a lower level of non-specific binding, in clinical term: "fewer side effects", than any other functional groups.

Tyrosine contains a phenolic side chain. Although the amino acid is only sparingly soluble in water, the ionizable nature of the phenolic group sometime makes it appear in hydrophilic regions of a protein—usually at or near the surface. Thus unlike cysteine residue, tyrosine derivatization proceeds without much need for deforming agents to further open the protein structure. Tyrosine may be targeted specifically for modification through its phenolate anion by acylation.

In summary, protein molecules may contain up to nine amino acids that are readily derivatizable at their side chains. These nine residues contain eight principal functional groups with sufficient reactivity for modification reactions. They are the guanidinyl group of arginine, the γ- and β-carboxyl groups of glutamic and aspartic acids, respectively, the sulfhydryl group of cysteine, the imidazolyl group of histidine, the ε-amino group of lysine, the thioether moiety of methionine, the indolyl group of tryptophan and the phenolic hydroxyl group of tyrosine. Since methionine and tryptophan are generally buried in the interior of proteins and are thereby protected from conjugates dissolved in the solvent, they show only some selected reactivity in intact proteins. The other ionizable groups are normally either exposed on the surface of proteins or can be accessed with the help of deforming agents or "drivers". They are therefore the easy targets for conjugation. However, among the numerous reactive functional amino acid side chains on the proteins that can be used for labeling, the sulfhydryl group of cysteine residue is most probably both pharmacologically and biologically important. It has been reported that in most macromolecules, there is at least one copy of reactive sulfhydryl group situated at or closed to the ligand binding sites of target macromolecules. Disruption of this reactive sulfhydryl functional group by sulfhydryl reducing agents has been shown to affect the functionalities of many macromolecules.

2.2. Moieties of Receptors Permitting Conjugation

The sulfhydryl moiety, with the thiolate ion as the active species, is the most reactive functional group in a protein. With a $pK_a$ of about 8.6, the reactivity of the thiol is expected to increase with increasing pH, toward and above its $pK_a$.

In the process of modifying a parent ligand, it is advantageous to capitalize the presence of this highly reactive sulfhydryl group, which is typically situated near or at the ligand-binding site of the receptor. Drugs or physiological ligands can be chemically modified to include a conjugation agent that reacts faster with the thiol group than any other reactive functional groups. Upon association of this modified drug with its receptor, this sulfhydryl group directed conjugate would attack any sulfhydryl group that is situated within its reachable proximity, this causes covalent binding of the drug to its receptor.

In addition to sulfhydryl group, there are also other highly reactive functional groups present on the amino acid side chains, which can be chemically modified. Conjugates that are reactive to these functional groups will be discussed below.

2.3. Conjugation Agents 2.3.1. Sulfhydryl Group Specific Conjugation Agents

N-Maleimide derivatives. Maleimides are considered fairly specific to the sulfhydryl group, especially at pHs below 7 where other nucleophiles are protonated. In acidic and near neutral solutions, the reaction rate with simple thiols is about 100-fold faster than with the corresponding simple amines. Although the rate increases with pH, the reaction with the amino group also becomes significant at high pHs. The other major competing reaction is the hydrolysis of maleimides to maleamic acids. However, at pH 7, the apparent rate of hydrolysis is only $3.2 \times 10^{-4}$ $min^{-1}$ in 0.1 M sodium phosphate buffer at 20° C., which is too slow to interfere with the reaction with sulfhydryl groups. The rate of decomposition becomes significant only at pH above neutrality. Thiol undergo Michael reaction with maleimides to yield exclusively the adduct to the double bond. The resulting thioether bond is very stable and cannot be cleaved under physiological conditions.

Disulfide reagents. Disulfide interchange occurs when sulfhydryl groups react with disulfides. Some of the most commonly used disulfide reagents are 5,5'-dithiobis-(2-nitrobenzoic acid), 4,4'-dithiodipyridine, methyl-3-nitro-2-pyridyl disulfide, and methyl-2-pyridyl disulfide. The protein disulfides formed are readily reverse in the presence of free mercaptan such as 0.2-mercaptoethanol or dithiothreitol. The reduction of protein disulfide into its original sulfhydryl group allows the protein to regain its functions. Thus, irreversible binding drugs of this category provide additional safety mechanism to counter various therapeutic complications such as over-dosing, hyper reaction, etc.

2.3.2. Amino Group Specific Conjugation Agents

The amino group is another strong nucleophile in the protein. However, because of its abundance and omnipresence in proteins, and the relatively high $pK_a$ of the ammonium ion, most of the reagents that react with the amino group can also react with other functionalities. Thus, it may not be an ideal target for modified ligands according to the invention, unless the critical cysteine residues are absent from the drug-binding site. Nevertheless, many stable acylated products are still and only formed with the amino groups. The most common reactions of amines are alkylation and acylation reactions. Some of the important alkylating agents that can be incorporated into ligand structures are: α-haloacetyl compounds (e.g., haloacetate, haloacetamides), N-maleimide derivatives, aryl halides (e.g., dinitrofluorobenzene, trinitrobenzenesulfonate), aldehydes (e.g., glutaraldehyde, formaldehyde) and ketones (e.g., pyridoxal phosphate). Acylating agents include, but are not restricted to, isocyanate, isothiocyanate, imidoesters, N-hydroyxlsuccinimidyl ester, p-nitrophenyl ester, acyl chloride, and sulfonyl chloride.

2.3.3. Carboxyl Group Specific Conjugation Agents

The most important chemical modification reactions of carboxyl groups utilize the carbodiimide-mediated process. With proteins, the optimum pH of the reaction is about 5, which is difficult to achieve in most physiological conditions. Other reagents such as diazoacetate esters and diazoacetamides can also be used to esterify carboxyl groups. Similar to carbodiinides, these reagents react with high specificity with carboxyl groups of proteins under mild acid conditions.

2.3.4. Tyrosine Specific Conjugation Agents

Tyrosine, histidine, and other aromatic residues of proteins are rich in electrons. These residues undergo electrophilic substitution reactions at the aromatic ring. Useful electrophiles for reaction with tyrosine and histidine in proteins are diazonium compounds. Other protein components such as lysine, tryptophan, cysteine, and arginine residues react very slowly, such that diazonium reagents can be regarded as tyrosine selective. Diazonium ions are generally unstable even at neutral pH and maximum reaction with the proteins is typically achieved at alkaline pH. The phenolate ion of tyrosine also reacts similar to amino groups toward acylating agents. However, the tyrosyl group is generally perceived as having a lower reactivity. This is not because the phenolate ion has lower nucleophilicity, but because tyrosine residues are usually buried in a protein and are, therefore, generally inaccessible for reactions due to their hydrophobicity.

2.3.5. Arginine Specific Conjugation Agents

A predominant reaction of the guanidinyl moiety of arginine residues is with 1,2-dicarbonyl reagents. Commonly used vicinal diketones include glyoxal, phenylglyoxal, 2-3-butanedione and 1,2-cyclohexanedione.

2.3.6. Histidine Specific Conjugation Agents

While a number of alkylating agents react with the imidazolyl moiety of histidines have been referred to earlier, the rate of these reactions is generally inferior to other nucleophiles. Even with α-haloacetate, N-carboxymethylation is generally slow in comparison with sulfhydryl groups. However, when such reactive α-halocarbonyl group is incorporated into affinity labels (e.g., p-toluenesulfonylphenylanine chloromethylketone, p-toluenesulfonyllysinechloromethylketone), specific reaction may be achieved. Beside α-haloacetyl groups, other alkylating agents are not as reactive towards histidine. With acylating reagents, histidine forms acylated products that are generally unstable and may undergo spontaneous hydrolysis. The most important acylating agent that has been commonly used for the modification of histidines is diethylpyrocarbonate or ethoxyformic anhydride. The acylated imidazole is reversed at alkaline pH, resulting in the recovery of histidine. Deacylation can be achieved at neutral pH very rapidly with hydroxylaimine.

2.3.7. Methionine Specific Conjugation Agents

The major chemical modification reaction of methionine is alkylation. Because methionine is often situated in the hydrophobic interior of proteins, it tends to provide high degree of selectivity. Only alkylating reagents that are coupled to the ligands are accessible to these buried methionine residues.

2.3.8. Tryptophan Specific Conjugation Agents

Due to its hydrophobicity, tryptophan residues are generally buried in the interior of proteins. Tryptophan residues can be modified with N-bromosuccinimide and 2-hydroxy-5-nitrobenzyl bromide. A distinct reagent, ρ-nitrophenylsulfenyl chloride, has been used for modification of the indolyl moiety. The reaction is selective for tryptophan and cysteine residues.

2.3.9. Serine Specific Conjugation Agents

Many reactive reagents such as diisopropylfluorophosphate, phenylmethyl-sulfonylfluoride and other acrylsulfonyl fluorides have been found to react with the active-site serine. Care should be exercised in use of such reagents because of the strong competitive reaction of hydrolysis.

2.4. Design of Modified Ligands of the Invention

The covalent bond formation between the modified ligand and the receptor can be catalyzed by enzymes, caused by activating agents, or facilitated by the conjugation agent on its own. The covalent bond is preferably formed with a functional group situated at or near the ligand-binding site of the receptor. This strategy is advantageous as it ensures a high degree of specificity.

The design of an irreversible binding ligand depends on the chemical, biological and molecular properties of both ligand and receptor. In each instance, the conjugation agent to be introduced onto the chemical structure of the ligand may be different and may require a certain configuration. In general, the ligand preferably includes a functional group which permits attachment of a conjugation agent, or which is capable of modification to contain such a group, without affecting the activity of the ligand to bind its receptor and to elicit a biological activity. The modified ligand in this regard need not have the same biological activity as the parent ligand (e.g., it may not require to be activated in vivo by some metabolic or catabolic step).

Some of the conditions and requirements to be considered for selection and configuration of the conjugation agent are as follows:

1. Determine reaction specificity towards a particular functional group of the receptor that is required for selection of the conjugation agent, e.g., amino, sulfhydryl, carboxyl, guanidinyl, imidazolyl, and other amino acid side chains. Selection will be dependent on the availability of any functional group on the receptor to which the drug molecule will be linked. The irreversible binding conjugation agent of the modified ligand must be specific to that functional group.

2. Hydrophobicity and hydrophilicity of the conjugation agent. A receptor in a hydrophobic environment may require a hydrophobic ligand to reach the receptor. For example, a modified ligand having a hydrophilic conjugation agent may not be able to access a corresponding functional group situated deep inside the hydrophobic core of the receptor.

3. Cleavability of the conjugation agent. It may be desirable in some cases to separate a modified ligand bound to a receptor. For example, if a toxic drug (corresponding to a parent ligand) is to be modified, a safety mechanism must be installed to preempt situations like over-dosing. In this case, the use of cleavable conjugation agents will enable the conjugation to be reversed if complication arises. A number of cleavable bonds may be employed for this purpose. These include disulfide bonds, amidine, mercurial group, vicinal glycol, azo, sulfone, ester and thioester linkages. In this regard, the conjugation agent itself may be cleavable or, if the conjugation agent is attached to the modified ligand through a spacer, the spacer may be cleavable. The spacer in this regard can be selected from the group consisting of (N-succinimidyl 3-(2-pyridyldithio)propionate, succinimidyloxycarbonyl-α-methyl-α-(2-pyridyldithio)toluene, 3-(2-pyridyldithio)propionyl hydrazide, disuccinimidyl tartarate, N-[4-(p-azidophenylazo)-benzyol]-3-aminohexyl-N'-oxysuccinimide ester, 4,4'-difuoro-3,3'-dinitrophenyl-sulfone, 3-(4-azido-2-nitrobenzoylseleno)propionic acid, 2-methylmaleic anhydride.

4. Size and geometry of the conjugation agent. Presence of the conjugation agent on a modified ligand must permit binding of that ligand to the receptor. Upon binding of the modified ligand to the receptor, the conjugation agent must be in close proximity to the receptor moiety so that conjugation is effected. A spacer as herein defined may be required to bring the conjugation agent in close proximity to the receptor moiety. In such a case, the length of the spacer will be dependent on the distance required for the conjugation agent to reach a conjugation-effective location adjacent to the receptor moiety. Structural analysis of receptor using X-ray crystallography, nuclear magnetic resonance and the like, combined with molecular modeling, can be of assistance in identifying the receptor moiety to be conjugated and in selecting and configuring the conjugation agent on the ligand chemical structure. The receptor moiety may be present in the ligand-binding site of the receptor. Preferably, the receptor moiety is present outside the ligand-binding site of the receptor. While not being limited to any theory, it is possible that this latter approach may be advantageous since it would be more likely to prevent disruption of receptor function upon binding with the modified ligand. On this basis, a parent agonist may be modified such that it crosslinks with its cognate receptor to thereby cause continuous stimulation of receptor function ("receptor turn-on"). Alternatively, a parent antagonist may be modified such that it crosslinks with its cognate receptor to thereby cause continuous inhibition of the receptor function ("receptor turn-off").

3. Compositions

The invention also encompasses a composition comprising the modified ligand as described herein, together with a pharmaceutically acceptable carrier.

The invention also features a method of treatment or prophylaxis of a condition associated with a target receptor, comprising administering to a patient in need of such treatment a therapeutically effective dosage of the composition as broadly described above.

Depending upon the particular route of administration, a variety of pharmaceutically acceptable carriers, well known in the art may be used. These carriers may be selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Any suitable route of administration may be employed for providing a patient with a composition of the invention. For example, oral, rectal, parenteral, sublingual, buccal, intravenous, intra-articular, intramuscular, intra-dermal, subcutaneous, inhalational, intraocular, intraperitoneal, intracerebroventricular, transdermal and the like may be employed.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of a modified ligand may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be effected by using other polymer matrices, liposomes and/or microspheres.

Compositions suitable for oral or parenteral administration may be presented as discrete units such as capsules, sachets or tablets each containing a pre-determined amount of one or more immunogenic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more modified ligands as described above with the carrier which constitutes one or more necessary ingredients. In general, the compositions are prepared by uniformly and intimately admixing the modified ligands of the invention with liquid carriers or finely divided solid carriers or both, and then, if necessary, shaping the product into the desired presentation.

The modified ligands may be in the form of a pharmaceutically acceptable salt as is known in the art.

The above compositions may be administered in a manner compatible with the dosage formulation, and in such amount as is therapeutically effective. In this regard, the dose of modified ligand administered to a patient should be sufficient to effect a beneficial response in the patient over time such as an amelioration of the condition to be treated. The quantity of the modified ligand(s) to be administered may depend on the subject to be treated inclusive of the age, sex, weight and general health condition thereof. In this regard, precise amounts of the modified ligand(s) for administration will depend on the judgement of the practitioner. In determining the effective amount of the modified ligand to be administered in the treatment or prophylaxis of the condition associated with the target receptor, the physician may evaluate progression of the condition.

In any event, those of skill in the art may readily determine suitable dosages of the modified ligands of the invention. Such dosages may be in the order of nanograms to milligrams of the modified ligands of the invention.

4. Detection of Target Receptors and Cells or Cell Membranes Containing Same The invention also features a method of detecting the presence of a target receptor in a test sample. The method comprises contacting the sample with a modified ligand as described in Section 2, wherein said modified ligand binds the target receptor, and detecting the presence of a complex comprising said modified ligand and said receptor in the contacted sample.

The invention also encompasses a method of quantifying the presence of a target receptor in a test sample. The method comprises contacting the sample with a modified ligand as broadly described above, wherein the modified ligand binds said target receptor, measuring the concentration of a complex comprising the modified ligand and the receptor in the contacted sample, and relating the measured complex concentration to the concentration of the receptor in the sample.

The invention also provides a method of detecting the presence of a target receptor on a cell or cell membrane. The method comprises contacting a sample containing the cell or cell membrane with a modified ligand as broadly described above, wherein the modified ligand binds the target receptor, and detecting the presence of a complex comprising the modified ligand and the cell or cell membrane in the contacted sample.

Also encompassed by the invention is a method of quantifying the presence of a target receptor on a cell or cell membrane. The method comprises contacting a sample containing the cell or cell membrane with a modified ligand as broadly described above, wherein the modified ligand binds said target receptor. The concentration of a complex comprising the modified ligand and the cell or cell membrane is then measured in the contacted sample, and the measured complex concentration is related to the concentration of the receptor present on the cell or cell membrane.

The modified ligands can be used as a tool to identify the actual drug pocket or drug binding area on the receptor molecules. Since the binding of these modified ligands to their targets is irreversible, the actual site that the drugs interact with can be identified on the receptors using various techniques such as peptide finger printing using Mass Spec. This information can be used to identify molecules that bind to that particular drug pocket.

Any suitable technique for determining formation of the complex may be used. For example, a modified ligand according to the invention, having a reporter molecule associated therewith (sometimes referred to herein as a "probe") may be utilised in any suitable assay known in the art for detecting and/or quantifying ligand-receptor interactions. For example, scintillation counting, autoradiography, fluorography, flow cytometry, UV spectroscopy, fluorescence spectroscopy, chemiluminescence imaging, fluorescence microscopy, confocal microscopy, electron microscopy, etc may be used in this regard.

The reporter molecule may be associated with the any suitable part of the modified ligand including the conjugation agent and the spacer, if included. Preferably association of the reporter molecule with the modified ligand is selected such that the reporter molecule does not interfere with binding of the modified ligand to the receptor.

It will be appreciated that the reporter molecule associated with the antigen-binding molecule may include the following:

direct attachment of the reporter molecule to the modified ligand;

indirect attachment of the reporter molecule to the modified ligand; i.e., attachment of the reporter molecule to another assay reagent which subsequently binds to the modified ligand; and attachment to a subsequent reaction product of the modified ligand.

The reporter molecule may be selected from a group including a chromogen, a chromophore, a catalyst, an enzyme, a fluorochrome, a chemiluminescent molecule, a lanthanide ion such as Europium ($Eu^{34}$), a radioisotope, a spin label, and a direct visual label.

In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes suitable for use as reporter molecules is disclosed in United States Patent Specifications U.S. Pat. No. 4,366,241, U.S. Pat. No. 4,843,000, and U.S. Pat. No. 4,849,338. Suitable enzymes useful in the present invention include alkaline phosphatase, horseradish peroxidase, luciferase, β-galactosidase, glucose oxidase, lysozyme, malate dehydrogenase and the like. The enzymes may be used alone or in combination with a second enzyme that is in solution.

Suitable fluorochromes include, but are not limited to, fluorescein isothiocyanate (FITC), tetramethylrhodamine isothiocyanate (TRITC), R-Phycoerythrin (RPE), and Texas Red. Other exemplary fluorochromes include those discussed by Dower et al. (International Publication WO 93/06121). Reference also may be made to the fluorochromes described in U.S. Pat. Nos. 5,573,909 (Singer et al), 5,326,692 (Brinkley et al). Alternatively, reference may be made to the fluorochromes described in U.S. Pat. Nos. 5,227,487, 5,274,113, 5,405,975, 5,433,896, 5,442,045, 5,451,663, 5,453,517, 5,459,276, 5,516,864, 5,648,270 and 5,723,218.

Preferably, the reporter molecule is a radioisotope such as $^3H$, $^{125}I$, $^{14}C$, $^{32}P$, $^{33}P$, and $^{35}S$.

5. Applications

Therapeutic. The modified ligands of the invention, which preferably represent irreversible binding drugs, have substantial advantages over conventional reversible binding drugs. Firstly, the dose-related inhibition or stimulation can be persisted long after the drugs disappear from the plasma In other words, the drug effect is likely to last longer than would be predicted from its plasma elimination half-life. Secondly, due to longer lasting drug effects, these irreversible binding drugs can be administered less frequently and at a lower dosage. This minimizes adverse side effect and prevent cumulative toxicity induce by the drug themselves or by their metabolites. Thirdly, since the binding of the irreversible antagonist to its receptor is permanent, the blockade of receptor response is not longer a competitive inhibition mechanism. This irreversible antagonism prevents the agonist, at any concentration, from producing a maximum effect on a given receptor. Furthermore, if the modified ligand is rendered highly radioactive, it may be used as a therapeutic for specifically killing cells bearing the cognate receptor or may be used for imaging.

Diagnostic. Another application of this ligand modification technology is to further elucidate various receptor subpopulations that can be targeted to relieve dysfunctions in the various complex physiological processes. More importantly, the modified drugs allow us to develop/identify animal models that are "deficient" in certain receptors without undergoing lengthy, tedious and complicated manipulation of the genetic materials. Hence the complex physiological mechanisms and functions of various receptors in "real-life" situations can be studied and analyzed. Furthermore, one can also study how the various different receptors are interlinked and influenced by each other's functions. The availability of such animal models will also enable investigators to predict and reveal therapeutic outcomes of various drugs by simultaneously blocking multiple receptor populations of interest. Thus, the present invention can be used to profile different receptors present on a cell as well as in a tissue, organ or system. Such receptor profiling can be used advantageously to discover novel drug targets, to predict the possible side-effects of drugs and to determine how various cells communicate with each other, their state of health, and whether they respond to certain external stimuli (e.g., to drugs).

The invention will now be described with reference to the following non-limiting examples.

EXAMPLES

Example 1

Effects of N-ethylmaleimide on the Equilibrative Nucleoside Transporter in Murine Myeloma SP2/0-Ag14 Cells.

Exemplary N-maleimide derivatives were used as a sulfhydryl reagent that is advantageously specific to the sulfhydryl group, reacting only with certain accessible sulfhydryl groups on the proteins, making it possible for specific inhibitions, and good penetration into cells due to the uncharged nature of the compound. N-Ethylmaleimide (NEM) is the smallest maleimide reagent capable of forming stable thio esters with the reactive sulfhydryl groups of proteins. The sensitivity of es and ei nucleoside transport systems towards NEM was demonstrated. Various different cell lines were used to show that the sensitivity of nucleoside transport system(s) toward NEM is a general phenomenon and not restricted to certain cell or tissues types.

Previous studies of the es nucleoside transporter system (Paterson et al. (1977), *Mol. Pharmacol.*, vol. 13, pp.114; Gati et al. (1983), *Mol. Pharmacol.*, vol. 23, pp. 146–1520) suggested that the sugar component of nucleosides was important for binding of a nucleoside to the es nucleoside transporter site. Thus in the present invention, that linker moiety was attached to the pyrimidine/purine ring of the nucleosides to avoid destruction of effective inhibition for the es nucleoside transporter to provide novel probes for that transporter regulatory site.

The present inventor has found that a novel group of nucleosides, cytidyl 4-[N-maleimidomethyl]cyclohexane-1-carboxylic acid (CrMCC) and derivatives and analogues thereof, have the ability to irreversible inhibiting the es nucleoside transporter proteins of human cells. A direct, rapid synthetic route used to synthesize CrMCC or 1-[[4-[(4-amino-1-β-D-ribofuranosyl-2(1H)-pyrimidione)carbonyl]cyclohexyl]methyl]-1H-pyrrole-2,5-dione, is set out in FIG. 3.

To demonstrate the sensitivity of es and ei nucleoside transport systems to NEM, various mammalian cell lines were treated with varying concentrations of NEM from 0 to 30 mM for 1 min prior transport assay. FIG. 1 shows the equilibrative transport (measured at 5 s uptake interval) of $^3$H-uridine (final concentration 50 µM) in murine myeloma SP2/0-Ag14 cells was inhibited by NEM in an apparent biphasic manner. About 60–70% of the transport activity was inhibited by NEM with $IC_{50}$ value of 0.15 mM. The remaining 30–40% of transport activity was gradually abolished by NEM at concentrations above 3 mM. Similar biphasic inhibition by NEM was also observed in human HL-60 and human MCF-7 cells, which possess both the es and ei transport systems (Lee et al. (1995), Biochim. Biophys. Acta, vol. 1268, pp. 200–208). For cells that possess only es (murine EL-4 cells) or only ei (rat Morris 7777) transport system, monophasic $^3$H-uridine transport curves in NEM dose-response experiments were observed. The $IC_{50}$ values were approximately 0.1 and 1.5 mM for EL-4 and Morris 7777 cells, respectively. These results suggested that the biphasic curve of total $^3$H-uridine transport observed in NEM dose-response experiments is a reflection of the presence of two distinct equilibrative nucleoside transport systems in those cells. The NEM-sensitive component is the es transport system and the NEM-insensitive component is the ei transport system. The ei transporter, although less sensitive to NEM inhibition, can be inhibited at higher concentrations of NEM or by prolonged exposure to NEM. This observation is in agreement with the general notion that sulfhydryl groups of enzymes display a considerable variation in their reactivity, ranging from unreactive, through several stages of sluggishness, to free and being immediately reactive.

Figure 2:
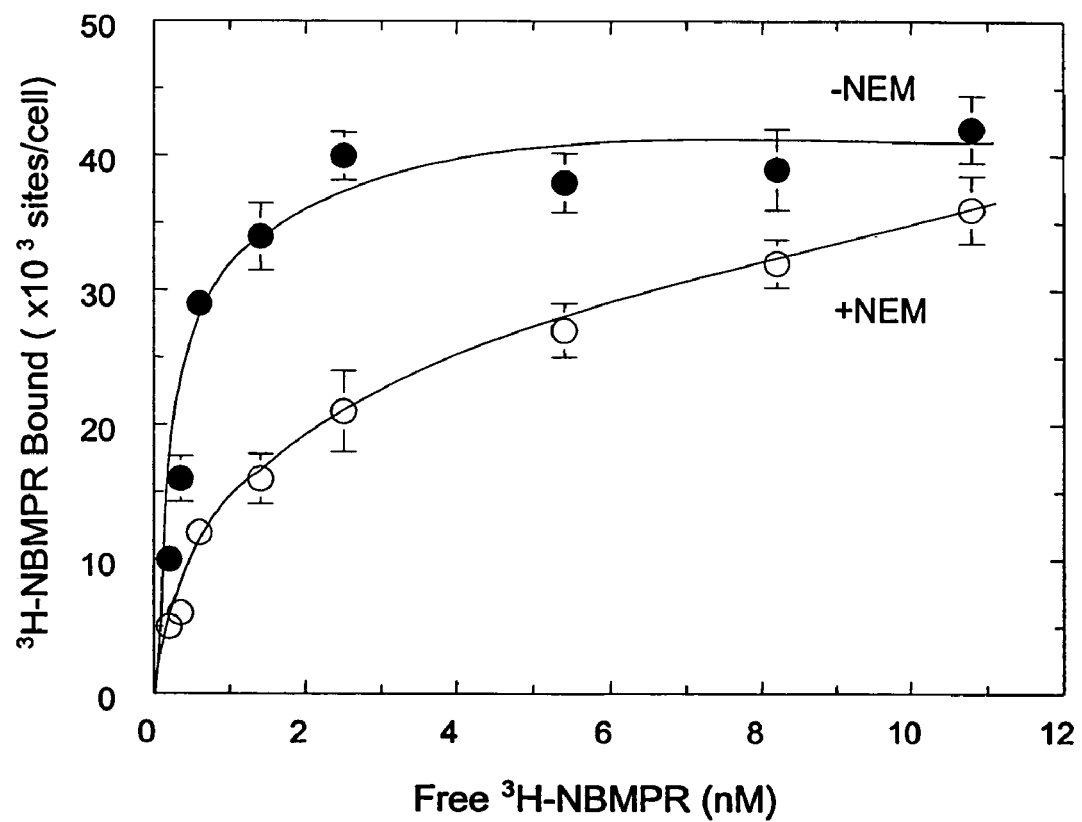
FIG. 2 shows the effects of NEM on the kinetics of $^3$H-NBMPR equilibrium binding in murine myeloma SP2/0-Ag14 cells.

To further demonstrate that the reduction in uridine influx by es transport system is due to NEM-induced chemical modification on the carrier protein which subsequently affected the transport affinity, and to confirm the notion that the changes in es nucleoside transport activity can be demonstrated by changes in $^3$H-NBMPR binding ability, murine myeloma SP2/0-Ag14 cells pretreated with or without 0.3 mM NEM for 1 min were assayed for the availability of high-affinity $^3$H-NBMPR binding sites on the cell membranes. FIG. 2 shows that the $K_d$ value (corrected for non-specific binding determined in the presence of 20 µM of NBTGR) for $^3$H-NBMPR binding was changed significantly in response to NEM treatment. Shortly after 1 min of NEM exposure, the apparent $K_d$ value was 1.9±0.4 nM, as compared to 0.16±0.02 nM for untreated cells. However, the $B_{max}$ values of 40,000±2,600 and 41,000±1,000 sites/cell for NEM treated and untreated cells, respectively, were not significantly different. These results provide additional evidence that a critical disulfhydryl bond is located near or close to the nucleoside transporting/binding site of the es transport system, where formation of disulfhydryl bond with NEM affects the transport affinity of the carrier. The suggestion that the critical sulfhydryl group on the es transporter protein is probably located or close to but not on the nucleoside transporting/binding site is derived from the observations that NBMPR, dilazep, dipyridamole at 30 µM and uridine at 10 mM were incapable of protecting this sulfhydryl group from NEM modification (Lee et al. (1995), Biochim. Biophys. Acta, vol. 1268, pp. 200–208). Although NEM is effective as an inhibitor of es transporter protein, it is toxic and should be modified for therapeutic purposes.

Example 2

Synthesis and Characterization of CrMCC

Figure 5:
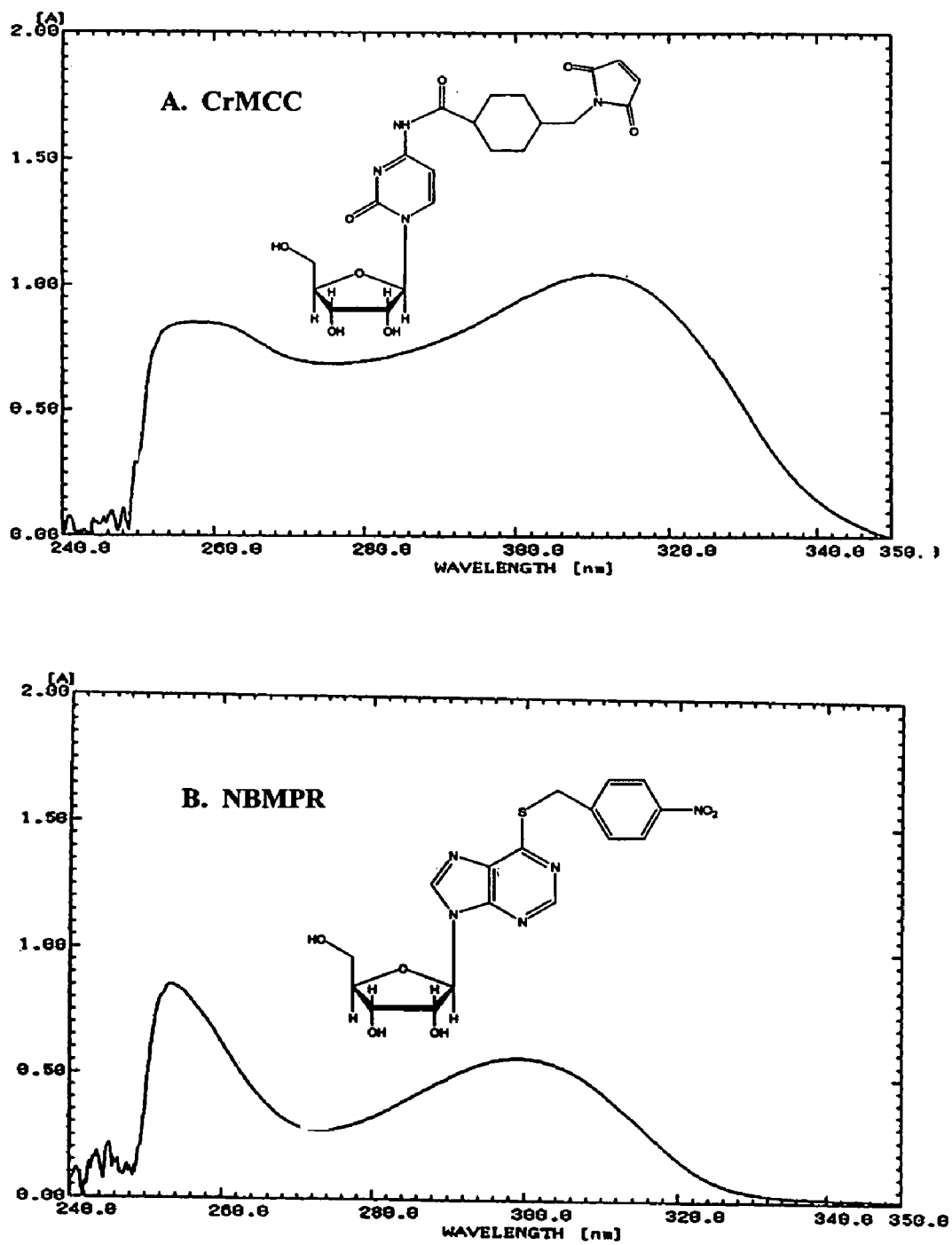
FIG. 5 shows the light absorbance profile of CrMCC and NBMPR.

The strategy to selectively irreversibly inhibit the es transporter protein is to attach a reactive group specific covalent binding agent (maleimide) to a driver so that it can deliver the covalent binding agent to the desired target. The most suitable driver will be the physiological ligand itself (nucleoside). Cytidine, a pyrimidine nucleoside, is selected among other physiological nucleosides due to its "function inertness", thus minimizes "non-specific" drug binding. As for the spacer arm that links the maleimide to the cytidine, a cyclohexane carboxylic acid is chosen for pilot studies. This configuration is to mimic the chemical structure of NBMPR (FIG. 5b). Furthermore, other advantages like hydrophobicity (provided by cyclohexane) and stability (provided by carboxylic acid) are also taking into consideration.

Figure 3:
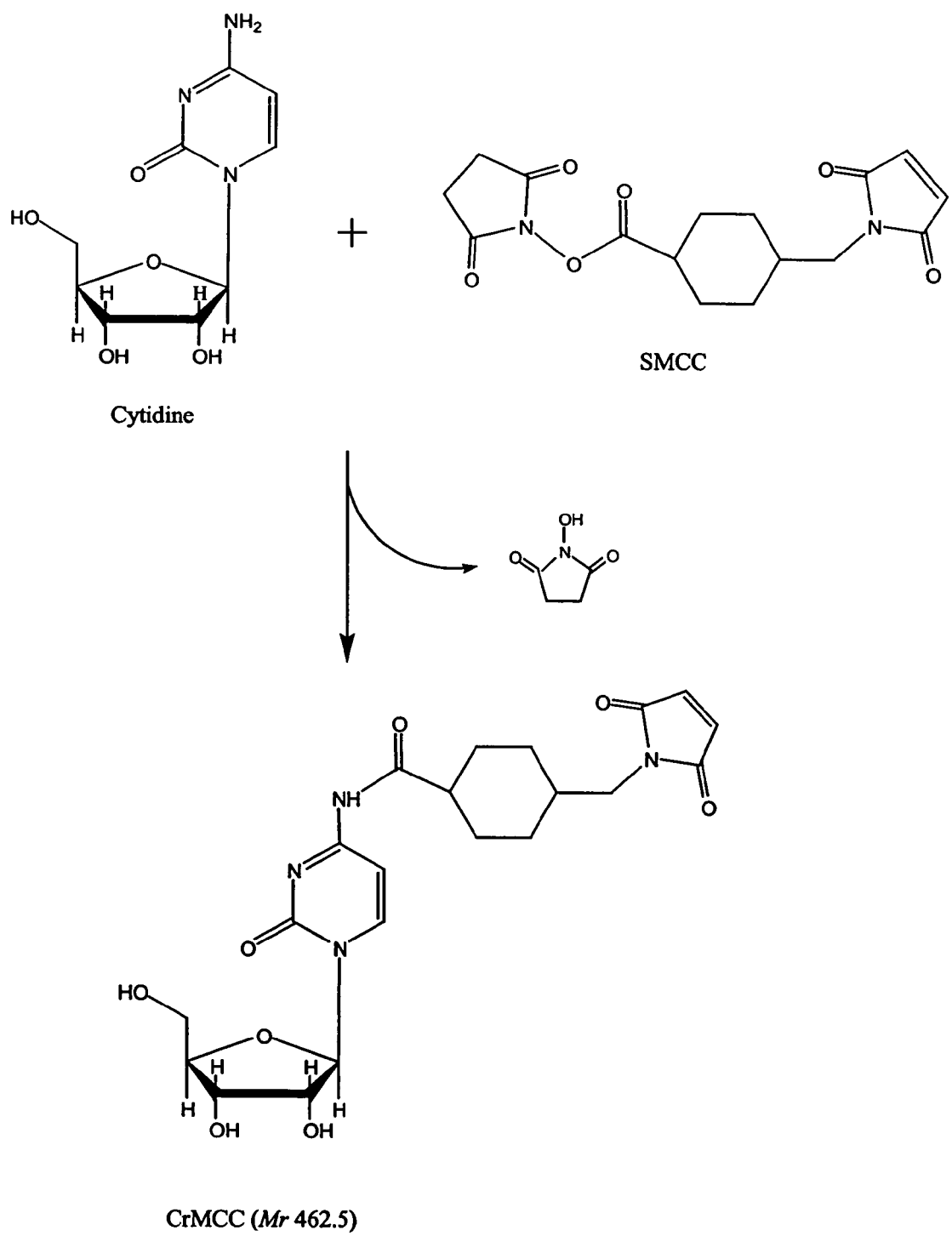
FIG. 3 shows the general reaction scheme for synthesis of CrMCC.

A direct, rapid synthetic route used to synthesize CrMCC or 1-[[4-[(4-amino-1-β-D-ribofuranosyl-2(1H)-pyrimidione)carbonyl]cyclohexyl]methyl]-1H-pyrrole-2,5-dione, is set out in FIG. 3.

Figure 4:
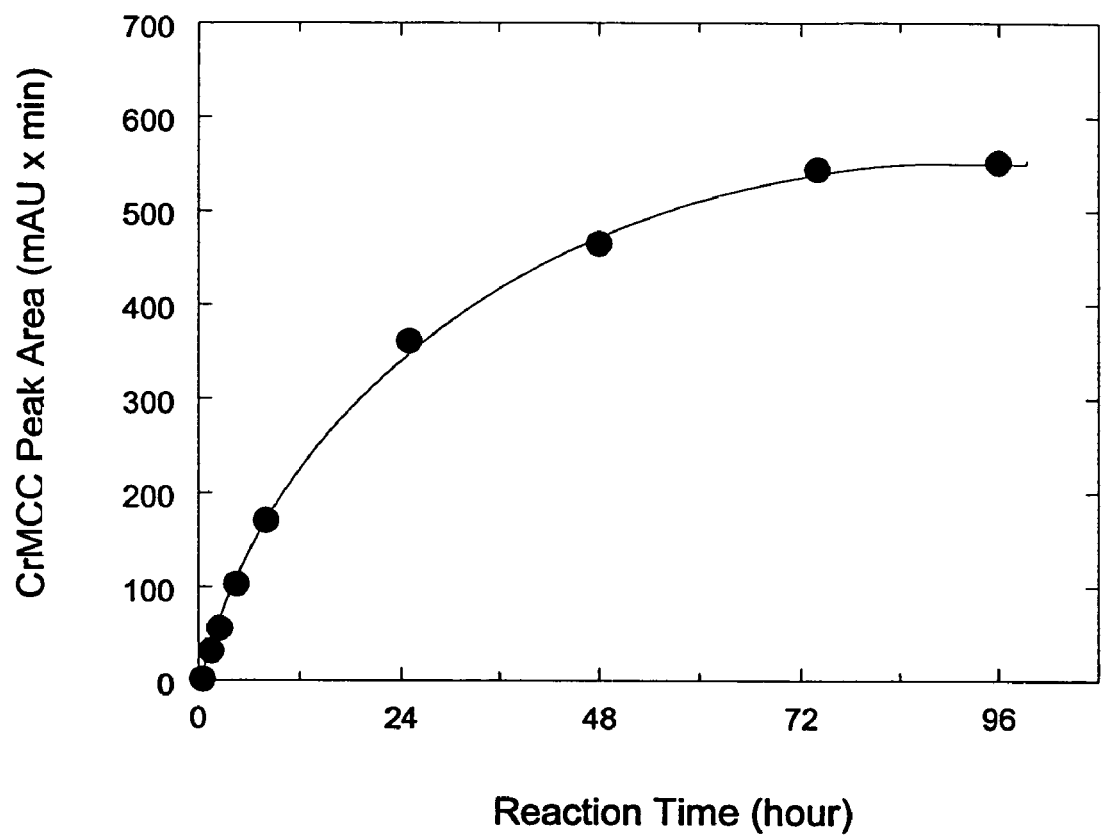
FIG. 4 shows the rate of CrMCC formation.

N-Succinimidyl 4-[N-maleimidomethyl]cyclohexane-1-carboxylate (SMCC) and cytidine were dissolved in anhydrous dimethysulfoxide (DMSO) separately prior reaction. The reaction started when these two reagents were mixed at room temperature and shielded from light. The molar concentration ratio of SMCC:cytidine in the mixture was 0.10 M:0.15 M with pH 7.5–8.0 in the reaction system. Within 4 hrs, CrMCC was found in the reaction mixture and can be separated from cytidine and SMCC by a $C_{18}$ reversed-phase column (Resource RPC, Pharmacia) operated on a HPLC (AKTA Purifier, Pharmacia) using the absorbance wavelength of 300 nm. Cytidine was eluted by 100% water and CrMCC and SMCC were eluted by 15% acetonitrile in water with the flow rate 1.5 ml/min. The hydrophobicity of CrMCC is greater than that of cytidine but is less than that of SMCC. Formation of CrMCC reached its near maximum after 48 hrs of reaction between SMCC and cytidine at 22–24° C. (FIG. 4). The area under the peak was calculated using a computer program UNICORN (version 2.0).

HPLC purified CrMCC was lyophilized by freeze-drying. The activity of CrMCC was stable for at least three months if it was stored at −20° C. in a desiccator. The molecular weight of CrMCC was determined by LC-MS (Waters). Briefly, CrMCC was eluted out of a $C_{18}$ reversed-phase column (Resource RPC, Pharmacia) by 20% acetonitrile in water at a flow-rate of 3 ml/min. The capillary voltage of micromass mass spectrometer was set to 3.0–3.5 V, and the cone voltage was set at 20 V. $N_2$ gas flow was at 700 L/hr and electrospray was negative. Mass spectra were gathered under a full-scan operation, scanning range 1–1000 m/z. The molecular weight of CrMCC was determined by monitoring the protonated molecular ion, and was similar to the predicted value of 462.5. The purity of CrMCC synthesized was consistently greater than 95%.

The light absorbance spectrum of CrMCC was measured by uv-vis spectrophotometer. FIG. 5A shows there are two $\lambda_{max}$'s for the light absorbance spectrum of CrMCC. One of them is at 254 nm (similar to the $\lambda_{max}$ of cytidine) and the other one is at 300 nm (similar to the $\lambda_{max}$ of SMCC). Such an absorbance profile of CrMCC with two $\lambda_{max}$'s is very similar to that of NBMPR (FIG. 5B). This indicated that CrMCC consists of both pyrimidine and cyclohexane rings on its chemical structure. Subsequent structural studies using NMR confirmed this finding.

Example 3

Effects of CrMCC on the Binding of ³H-NBMPR in human HL-60 Promyelocytic Leukemia Plasma Membranes To synthesize ³H-CrMCC, radioactive cytidine (3H-cytidine) was used. Since high concentration of substrate increases the yield of CrMCC, non-radioactive cytidine was pre-mixed with radioactive ³H-cytidine at a concentration ratio of 100:1 prior to reaction with SMCC (see Example 2).

Figure 6:
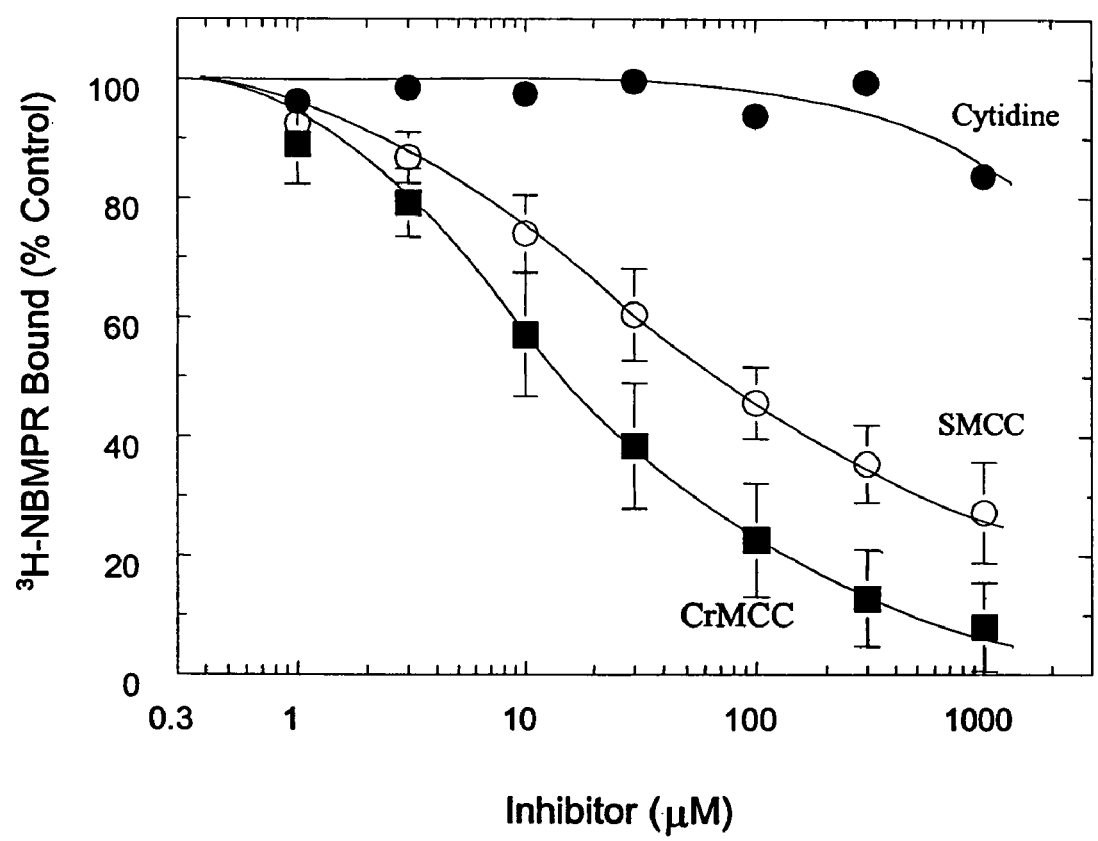
FIG. 6 shows the inhibition of $^3$H-NBMPR binding by CrMCC, cytidine and SMCC in human HL-60 promyelocytic leukemia plasma membranes.

Purified HL-60 plasma membranes suspended in reaction buffer (0.13 M NaCl, 0.02 M NaHCO₃, pH 7.0) were pretreated with graded concentrations of cytidine, SMCC, and CrMCC for 5 min prior exposed to ³H-NBMPR (5 nM) for additional 30 min. The reaction was terminated by membrane filtration method (Lee & Jarvis (1988), *Biochem. J.*, vol. 249, pp. 557–564). The data shown in FIG. 6 were corrected for non-specific binding determined in the presence of 20 μM of NBTGR. FIG. 6 shows the specific of ³H-NBMPR to HL-60 unsealed plasma membranes was inhibited by CrMCC with $IC_{50}$ value of 10 μM. In contrast, the $IC_{50}$ values for SMCC and cytidine in inhibiting ³H-NBMPR binding were 100 μM and >1 mM, respectively. The $K_i$ value for CrMCC was calculated to be 1 μM.

Figure 7:
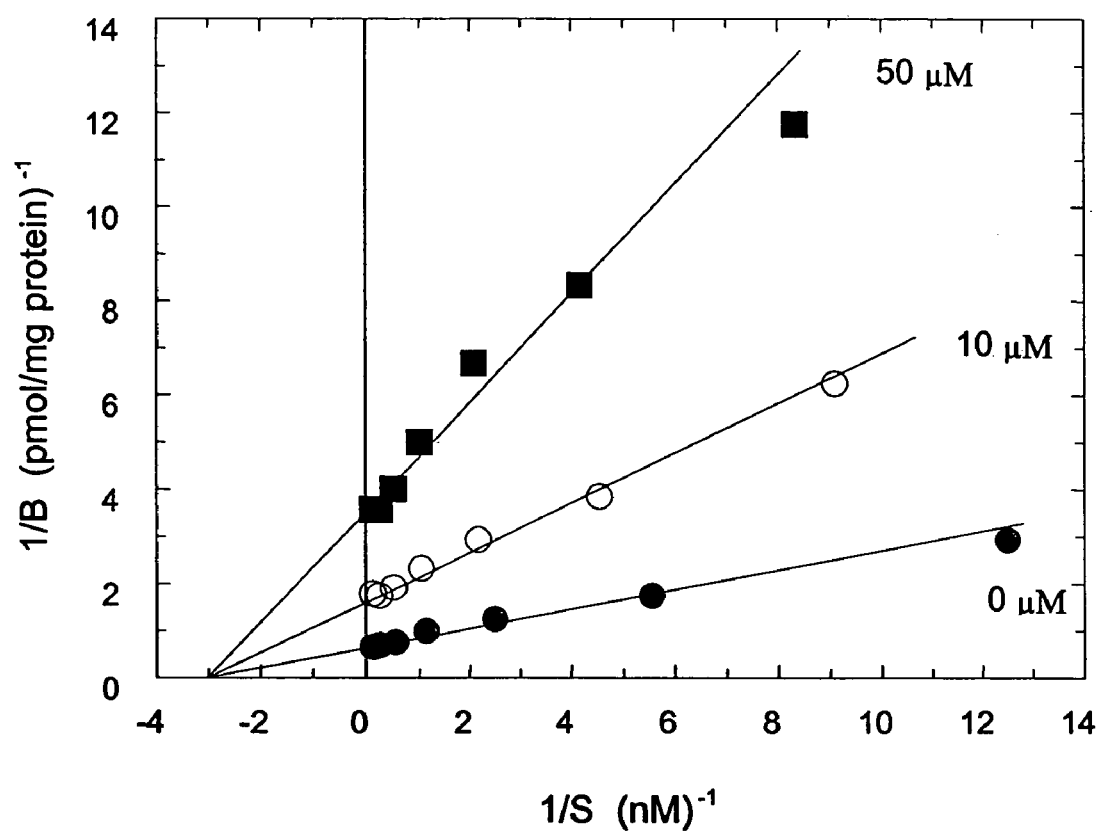
FIG. 7 shows the effect of CrMCC on the kinetics of $^3$H-NBMPR binding to human HL-60 promyelocytic leukemia plasma membranes.

To analyse the effect of CrMCC on the binding kinetics of ³H-NBMPR, purified HL-60 plasma membranes were pretreated with 0, 10, and 50 μM of CrMCC for 5 min prior incubated with graded concentrations of ³H-NBMPR (0.2 to 8 nM) for additional 30 min. A double reciprocal plot of the results is presented in FIG. 7. The lines of the plots were intersected at the abscissa indicating a changed value for $B_{max}$ but an unchanged value for $K_d$ in the presence of CrMCC. For the data shown, the apparent $K_d$ values of ³H-NBMPR binding were 0.36±0.04, 0.31±0.03 and 0.39 ±0.05 nM with $B_{max}$ values of 1.56±0.05, 0.59±0.01 and 0.30±0.01 μmol/mg protein for membranes treated with 0, 10 and 50 μM of CrMCC, respectively. Data were corrected for non-specific binding determined in the presence of 20 μM of nitrobenzylthioguanosine (NBTGR), a non-radioactive competitive ligand. These results suggested a non-competitive inhibition of ³H-NBMPR binding by CrMCC. This is a unique feature of the irreversible antagonism.

Figure 8:
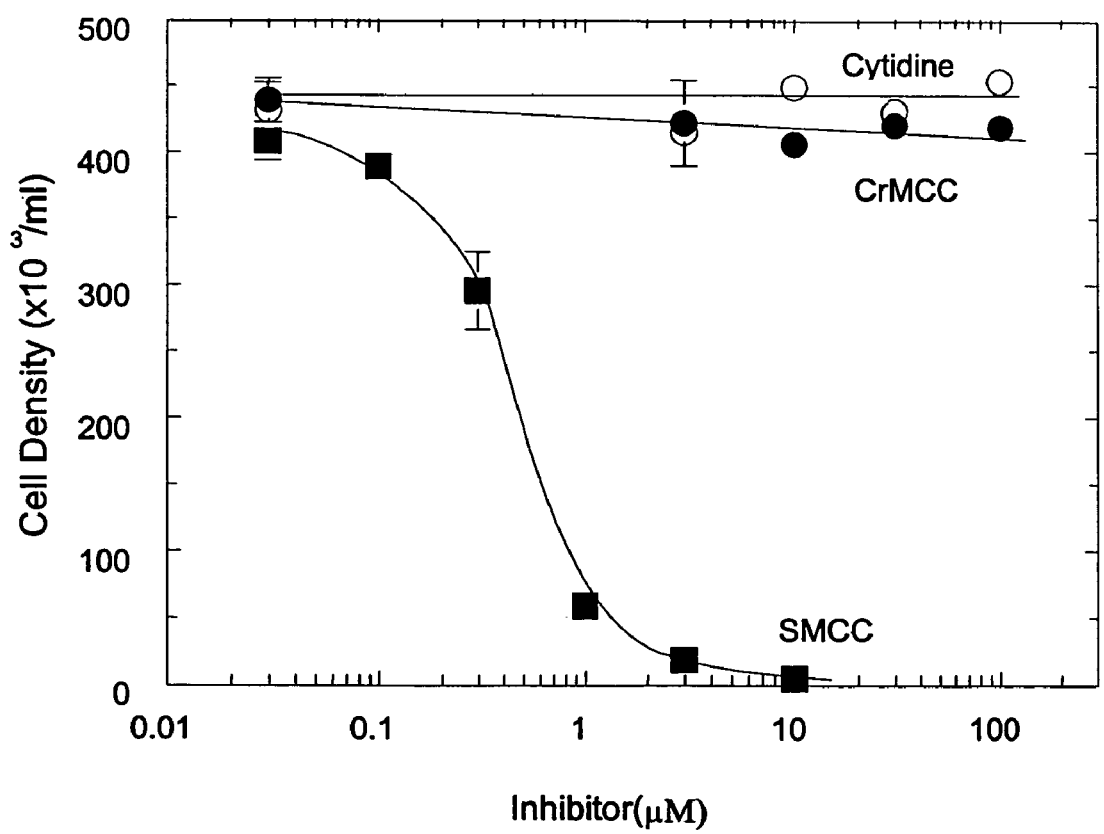
FIG. 8 shows the effects of CrMCC, cytidine and SMCC on growth of HL-60 cells.

Any clinically useful drugs must have little or no cytotoxicity at their therapeutic dosage range. HL60 cells in logarithmic growth at an initial cell density of 5×10⁴ cells/ml in RPMI medium containing 10% FBS were exposed to graded concentrations of CrMCC, cytidine, and SMCC (0 to 100 μM) for 3 days. The cell density was counted using an electronic particle analyzer (Sysmex). FIG. 8 shows both CrMCC and cytidine had little or no effect on HL-60 cell growth at concentrations as high as 100 μM after 3 days of exposure. In contrast, SMCC, one of the parent compounds, was extremely toxic to HL-60 cells with $IC_{50}$ value of less than 0.5 μM on cell growth. The toxicity of SMCC is attributed to its non-specific interaction with every accessible sulfhydryl groups on the cells. Little or no inhibition on cell growth by cytidine is expected as this nucleoside is rather "inert" and does not induce nucleotide imbalance at concentration range tested.

Example 4

Binding of ³H-CrMCC to the Human HL-60 Promyelocytic Leukemia Plasma Membranes

Figure 9:
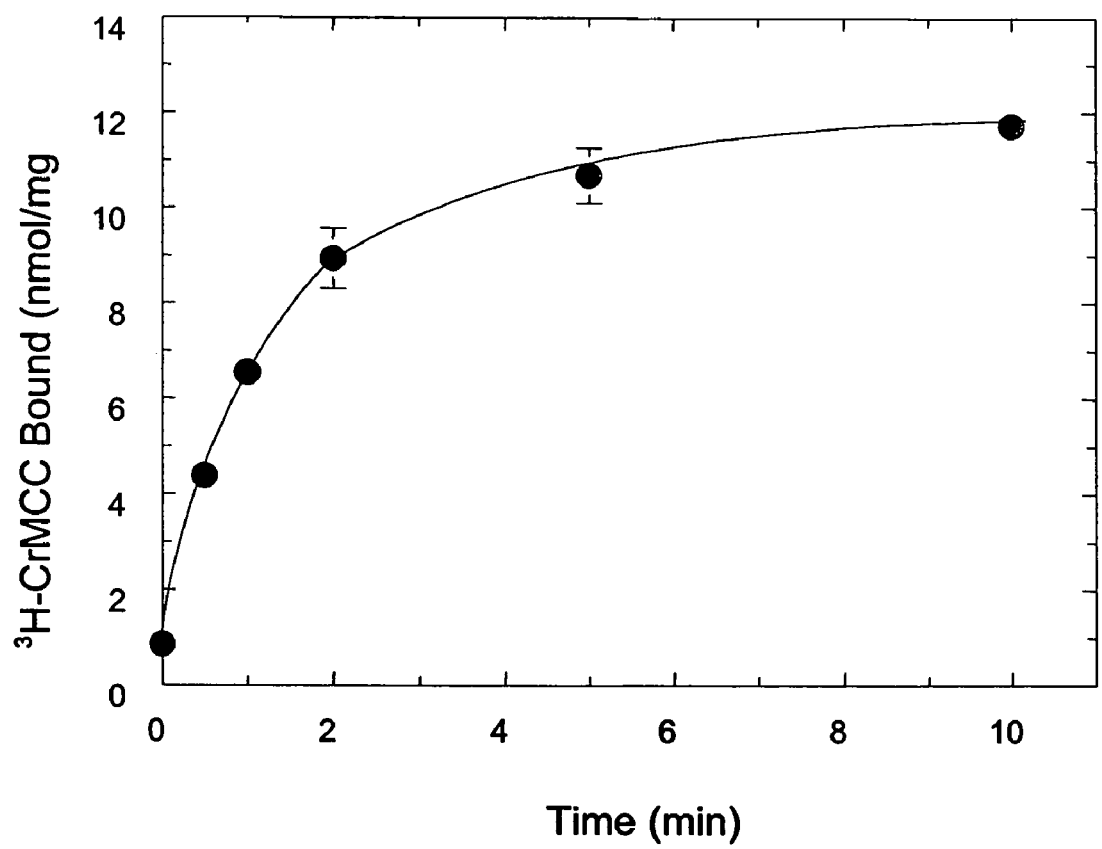
FIG. 9 shows the time course of $^3$H-CrMCC binding to human HL-60 promyelocytic leukemia plasma membranes.

The availability of radioactive CrMCC (³H-CrMCC) makes it possible to study the biochemical properties of CrMCC on the es nucleoside transporter. This experiment was conducted to investigate the rate of ³H-CrMCC binding to the unsealed plasma membranes of HL-60 cells. FIG. 9 shows the binding of ³H-CrMCC (30 μM final concentration) to purified HL-60 plasma membranes was rather slowed. A minimum of 5 min is needed to achieve the maximum binding value of 12 mmoles per mg of HL-60 plasma membrane protein. This is unlike the binding of reversible antagonists such as NBMPR, dipyridamole and dilazep, which the binding was known to be rapid and mostly completed within first minute of incubation. The binding reaction in FIG. 9 was terminated by membrane filtration method and the data were corrected for filter blanks.

Figure 10:
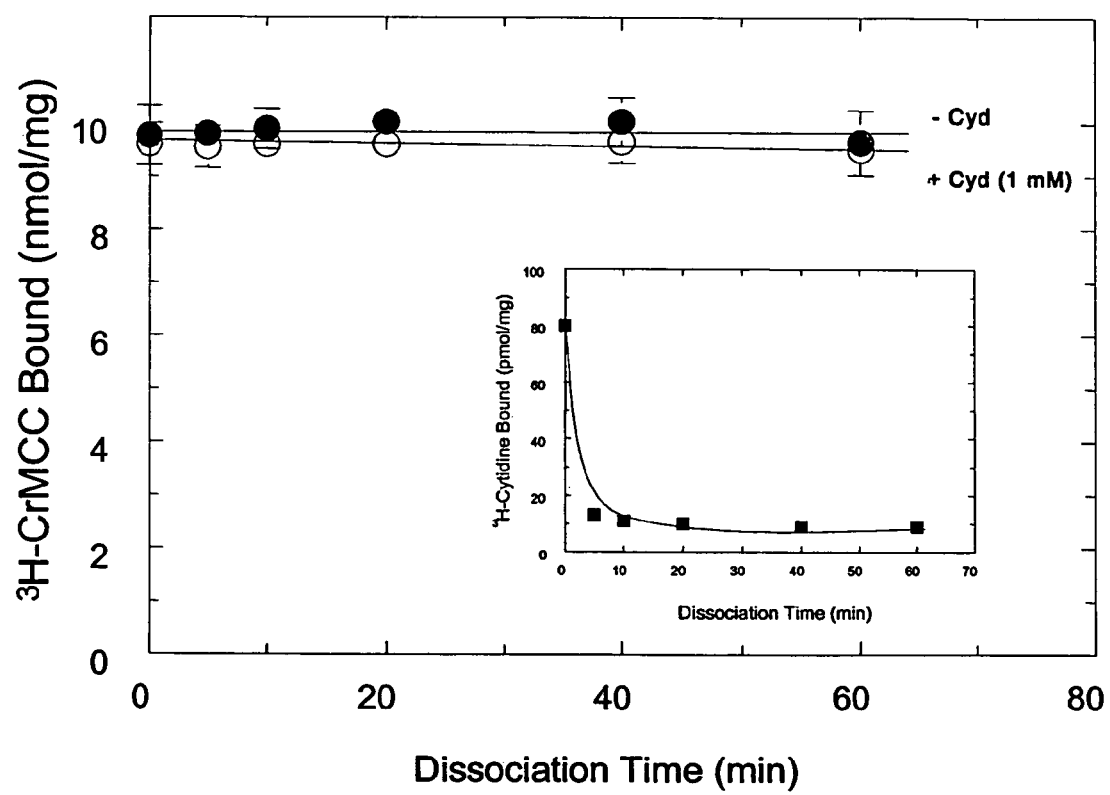
FIG. 10 shows the dissociation of $^3$H-CrMCC and $^3$H-cytidine from the binding sites of human HL-60 promyelocytic leukemia plasma membranes.

It is important to confirm the binding of ³H-CrMCC to the unsealed HL-60 plasma membranes is indeed irreversible. Purified unsealed HL-60 plasma membranes were incubated with 30 μM of ³H-CrMCC for 10 min. After which the mixtures were diluted 20 folds and the diluted mixtures were sat at room temperature for various time intervals to allow dissociation to occur. FIG. 10 shows little or no dissociation of ³H-CrMCC from its binding sites occurred for at least 60 min after a 20-fold dilution. Even 1 mM of cytidine presence in the dilution medium failed to displace ³H-CrMCC from its binding sites. In contrast, the binding of 30 μM of ³H-cytidine to HL-60 plasma membranes was low and dissociated rapidly and completely upon dilution (inset of FIG. 10). This finding together with the non-competitive inhibition of ³H-NBMPR binding by CrMCC (FIG. 7) suggested the interaction of CrMCC to its binding sites is indeed irreversible. The dissociation reaction shown in FIG. 10 was terminated by membrane filtration method and the data were corrected for filter blanks.

Figure 11:
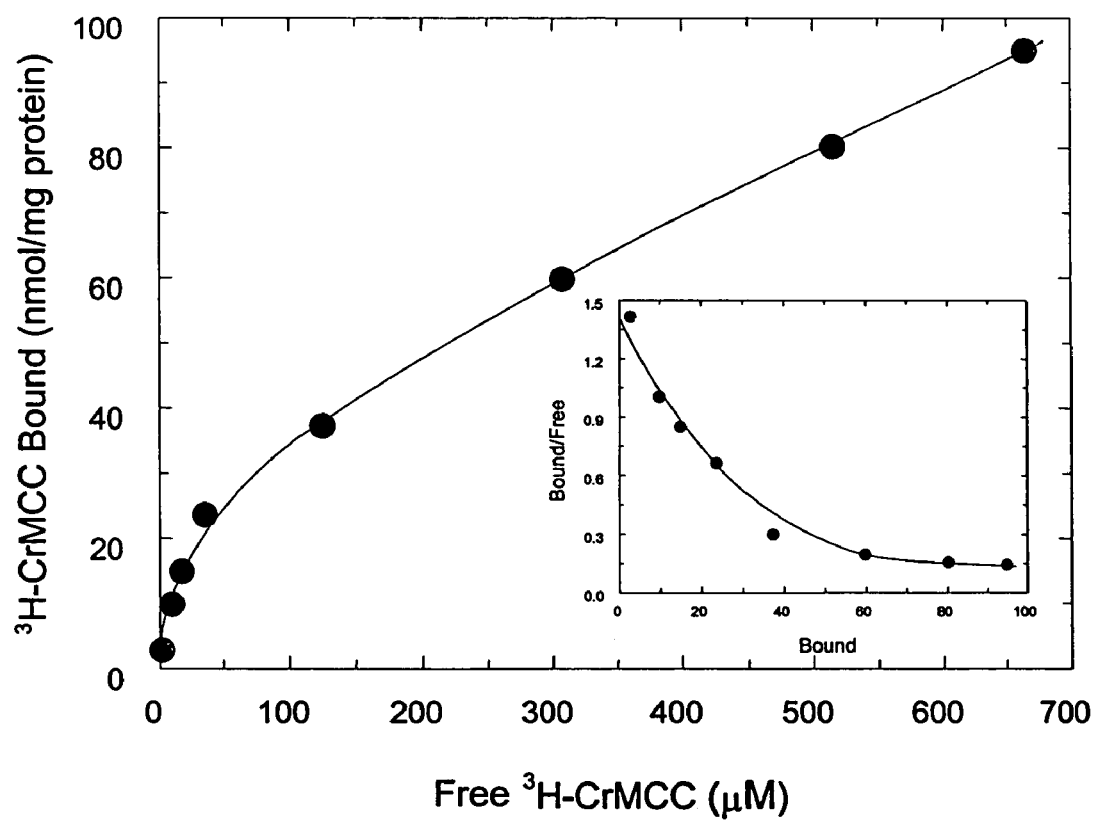
FIG. 11 shows the concentration dependence of $^3$H-CrMCC binding to human HL-60 promyelocytic leukemia plasma membranes.

To determine the concentration dependence of ³H-CrMCC binding to its binding sites, purified unsealed HL-60 plasma membranes were incubated with graded concentration of ³H-CrMCC (3 to 800 μM) for 10 min and the reaction was terminated by membrane filtration method (FIG. 11). The data can be resolved into at least two components, a high affinity component ($K_d$=23.8±2.2 μM) and a low affinity component (inset of FIG. 11). The kinetic constants for the low affinity component cannot be estimated with the existing concentration range of ³H-CrMCC. It is also possible that this low affinity component is a non-specific ³H-CrMCC binding site. The data shown in FIG. 11 were corrected for filter blanks.

Figure 12:
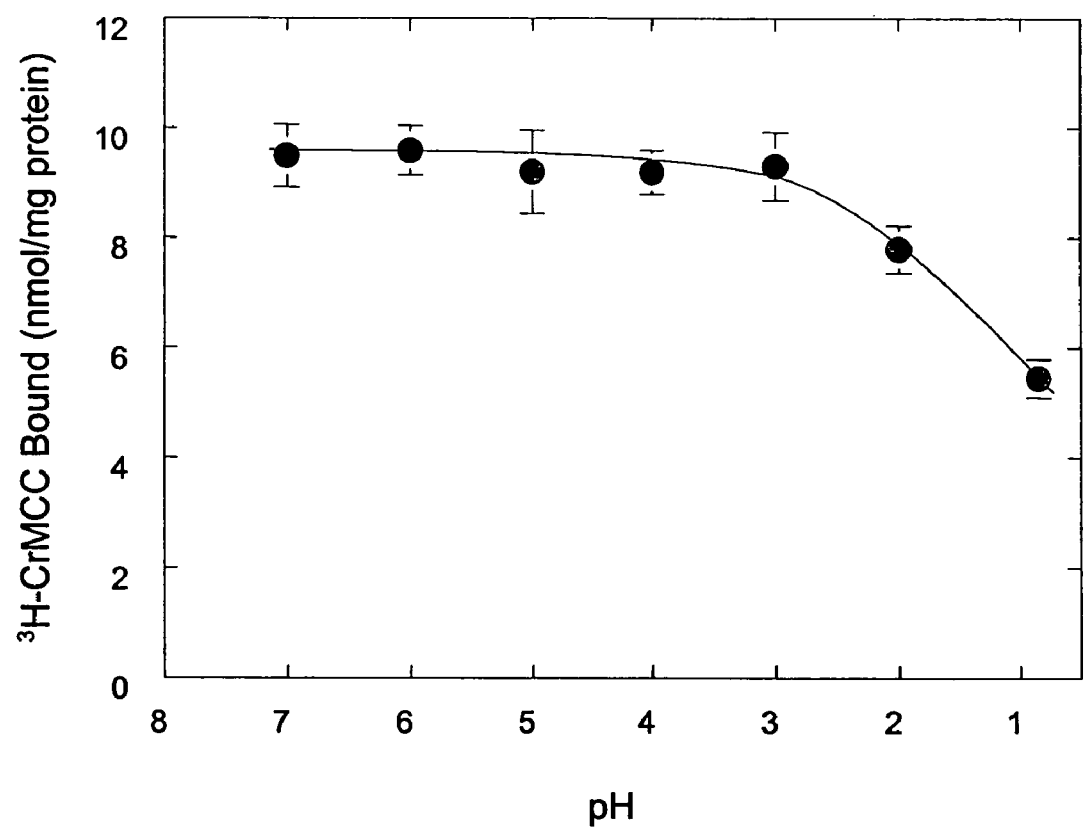
FIG. 12 shows the effect of pH on the dissociation of $^3$H-CrMCC from its binding site in human HL-60 promyelocytic leukemia plasma membranes.

It is important to determine the stability of ³H-CrMCC-receptor complexes in various pH conditions. Purified unsealed HL-60 plasma membranes were incubated with 30 μM of ³H-CrMCC for 5 min. The reaction mixture was then diluted 20-fold with reaction buffer of various pH values (pH 0.85 to 7.5). The dissociation reaction was terminated by membrane filtration method. The data were corrected for filter blanks. FIG. 12 shows ³H-CrMCC-receptor complexes were very stable at physiological pH. However, the ligand-receptor complexes began to break down at pH below 3.5.

Figure 13:
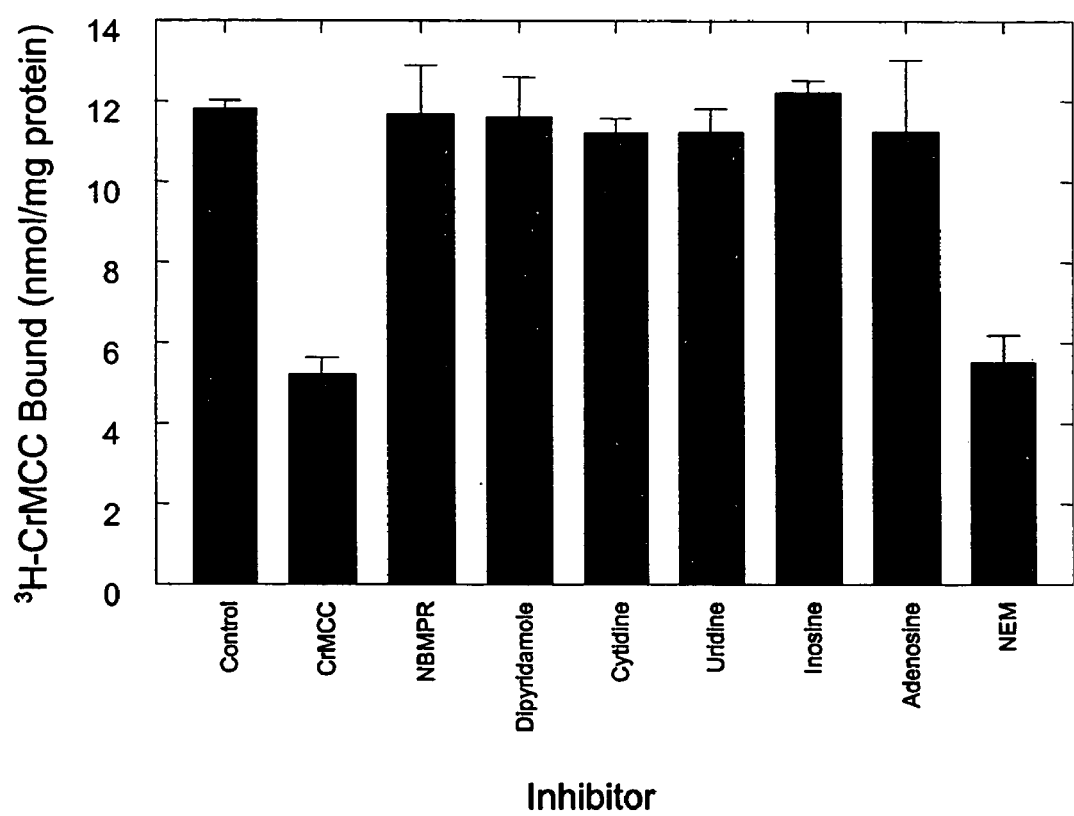
FIG. 13 shows the inhibition of $^3$H-CrMCC binding to human HL-60 promyelocytic leukemia plasma membranes.

Early studies with sulfhydryl reagent NEM had suggested that a cysteine residue is probably situated very close to but not on the nucleoside transporting/binding site of the es nucleoside transporter protein. Thus, if ³H-CrMCC is bind to the same site that NEM binds, then the substrates that failed to inhibit NEM action (Lee et al. (1995), *Biochim. Biophys. Acta*, vol. 1268, pp. 200–208) should similarly have little or no effect on ³H-CrMCC binding. FIG. 13 shows 1 mM of physiological nucleosides (e.g. cytidine, uridine, adenosine and inosine), and 20 μM of es nucleoside transport inhibitors (e.g. NBMPR and dipyridamole) indeed failed to inhibit the binding of ³H-CrMCC (30 μM final concentration) to the HL-60 plasma membranes. In contrast, 1 mM of NEM was as effective as 0.5 mM of CrMCC in inhibiting the binding of $^3$H-CrMCC. This finding suggested that NEM and CrMCC reacted to the same sulfhydryl group on the es nucleoside transporter protein.

Example 5

Figure 14:
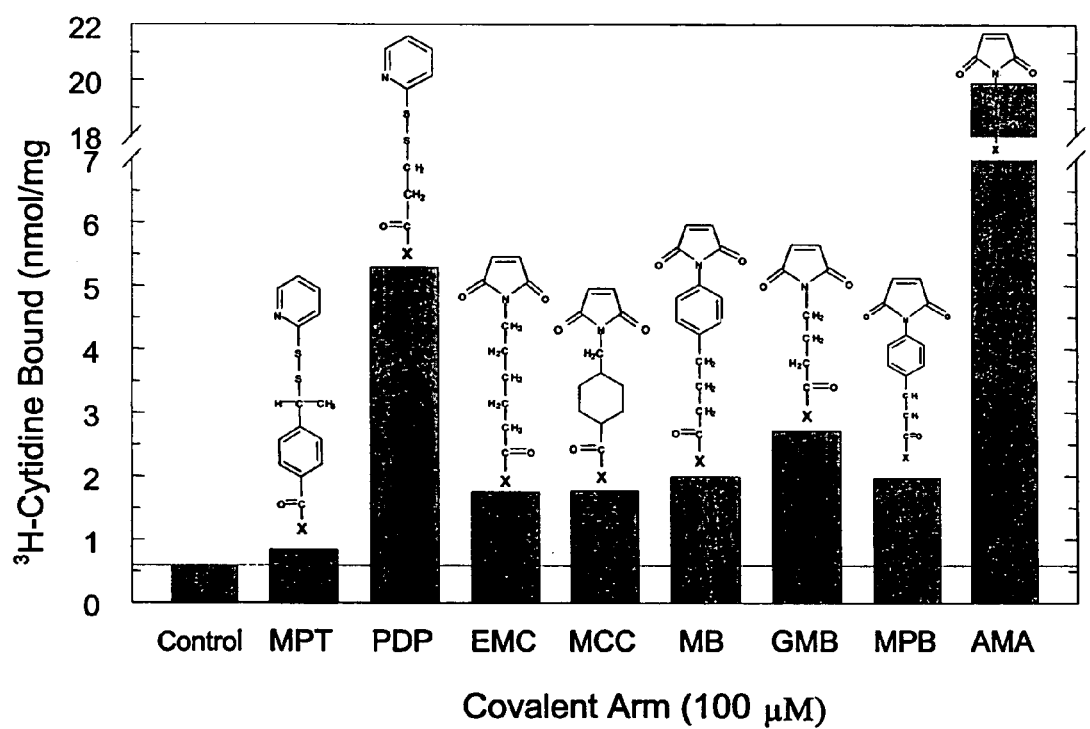
FIG. 14 shows the covalent binding of sulfhydryl reactive $^3$H-cytidine analogs to human HL-60 promyelocytic leukemia plasma membranes.

Effects of Other Sulfhydryl Reactive Covalent Arms on the Binding of $^3$H-Cytidine Molecule to Human HL-60 Promyelocytic Leukemia Plasma Membranes It was successfully demonstrated that maleimide, a sulfhydryl group reactive agent, linked to cytidine via a cyclohexane carboxylic acid spacer arm is effective in irreversibly inhibiting the binding of $^3$H-NBMPR to the es transporter protein. In this experiment, the binding capability of $^3$H-cytidine molecule to the HL-60 plasma membranes after being linked to the same or different sulfhydryl group reactive agent via different spacer arms was compared, to provide an indirect indication on the suitability of the spacer arms used in creating the irreversible es nucleoside transport inhibitor. Thus, $^3$H-cytidine was chemically modified to incorporate various sulfhydryl reactive side arms onto the 6-amino position of the pyrimidine ring. Chemicals used to modify $^3$H-cytidine include m-maleimidobenzoyl-N-hydroxysuccinimide (MBS), N-succinimidyl 4-[p-maleimidophenyl] butyrate (SMPB), N-[γ-maleimidobutyryloxy]succinimide, 4-succinimidyloxycarbonyl-α-methyl-α-[2-pyridylthio] toluene (SMPT), N-succinimidyl 3-[2-pyridyldithio]propionate (SPDP), N-succinimidyl maleimidoacetate (AMAS), and N-[α-maleimidocaproyloxy]succinimide (EMCS), in addition to N-succinimidyl 4-(N-maleimidomethyl)cyclohexane-1-carboxylate (SMCC). Purified HL-60 plasma membranes were incubated with 100 μM of these chemically modified $^3$H-cytidine analogs for 5 min. The reaction was terminated by membrane filtration method. FIG. 14 shows N-α-maleimidoacetoxylic acid (AMA) covalent arm promotes highest irreversible binding of $^3$H-cytidine to the HL60 plasma membranes followed by 3-[2-pyridyldithio] propionic acid (PDP). However, N-s-maleimidocaproylic acid (EMC), m-maleimidobenzoic acid (MB), N-γ-maleimidobutyrylic acid (GMB) and 4-[p-maleimidophenyl]butyrylic acid (MPB) were equally effective as covalent arms as compare to N-maleimidomethyl cyclohexane carboxylic acid (MCC). In contrast, α-methyl-α-[2-pyridyldithio]toluene carbonic acid (MPT) was least effective. Symbol X in FIG. 14 represents cytidine.

Example 6

Figure 15:
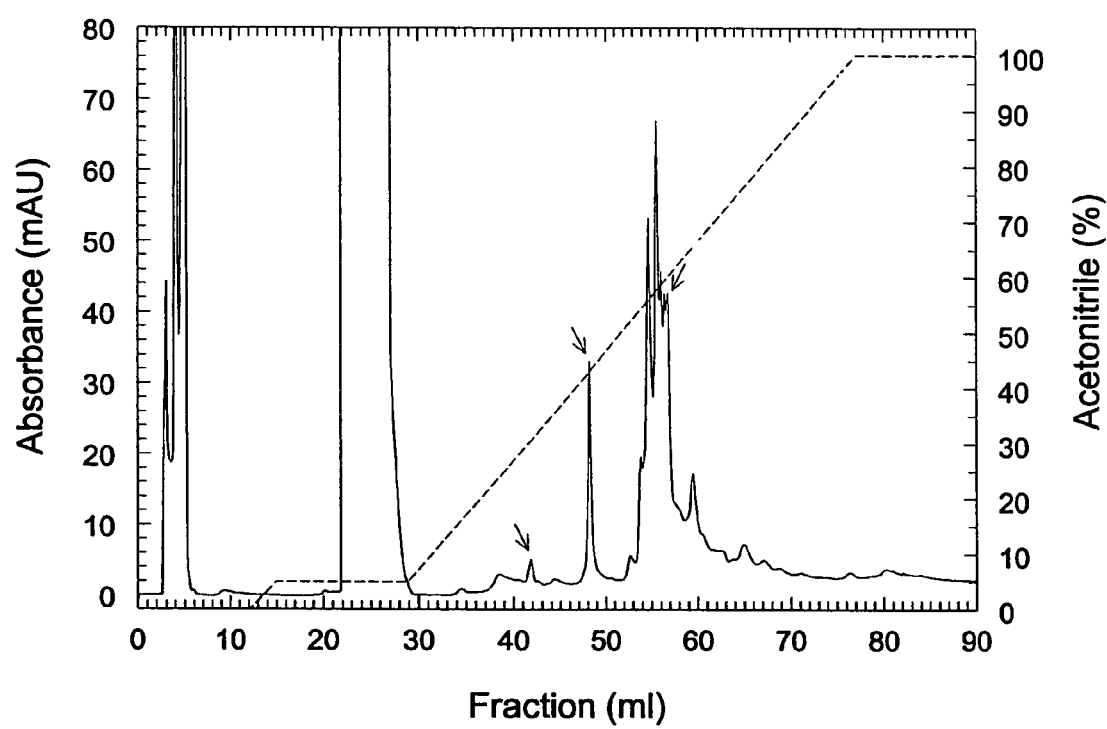
FIG. 15 shows the UV absorbance profile of reversed-phase chromatography of human HL-60 promyelocytic leukemia plasma membrane proteins.
Figure 16:
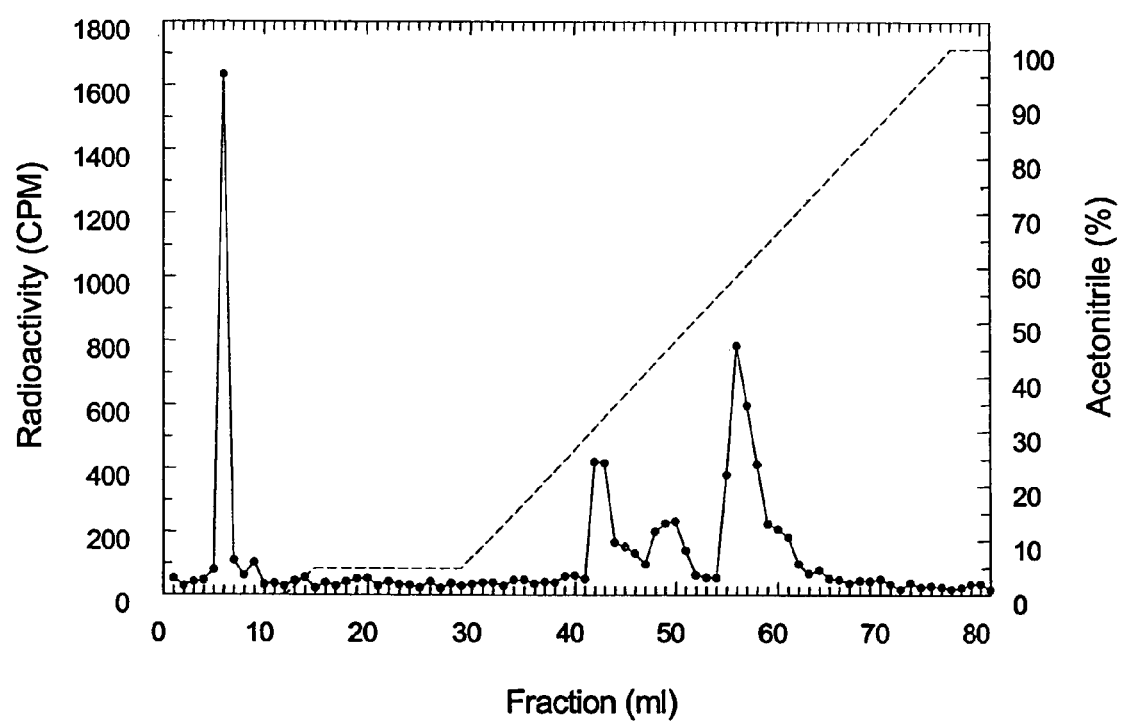
FIG. 16 shows the radioactivity profile of reversed-phase chromatography of human HL-60 promyelocytic leukemia plasma membrane proteins.

Identification of $^3$H-CrMCC Binding Proteins in Human HL-60 Promyelocytic Leukemia Plasma Membranes Attempts were made to identify the plasma membrane proteins that were labelled by $^3$H-CrMCC. $^3$H-CrMCC (20 μM) labelled HL-60 plasma membrane proteins solubilized in SDS were loaded onto a $C_{18}$ reversed-phase column (Resource RPC, Pharmacia) operated on a FPLC (ATKA FPLC, Pharmacia) with the following conditions: column volume (CV, 3 ml), starting buffer A (0.05% TFA in water), eluent B (0.065% TFA in acetonitrile), flow rate (2 ml/min), detection (280 nm), elution (0% B in 3 CV, 0–5% B in 1 CV, 5% B in 5 CV, 5–100% B in 15 CV, wash-out 100% B). FIG. 15 shows the general UV (k=280 nm) absorbance profile of HL-60 plasma membranes after being separated by FPLC using a $C_{18}$ reversed-phase column. The arrows on the chromatogram indicate the protein peaks that were labelled by $^3$H-CrMCC (refer to FIG. 16). The eluents were collected at 1 ml/min and the radioactivity was determined by a liquid scintillation counter. FIG. 16 shows there are at least three major radioactive peaks located at fraction numbers 43–44, 49–50, and 57–59 of the chromatogram. The sharp radioactive peak at fraction number 6 is due to degradation product of $^3$H-CrMCC (i.e. $^3$H-cytidine) and the non-specific binding of $^3$H-CrMCC to the membrane lipids.

Example 7

Development of Irreversible Binding Drugs of Adenosine Origin

Figure 17:
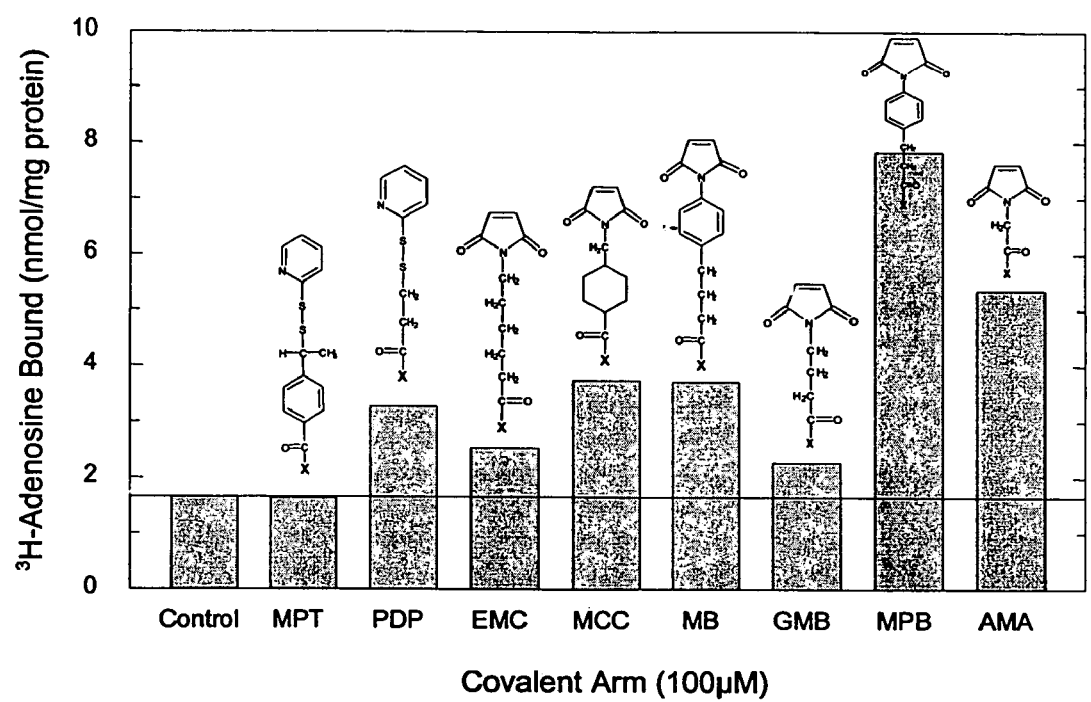
FIG. 17 shows the covalent binding of sulfhydryl group reactive $^3$H-adenosine analogs to human HL-60 promyelocytic leukemia plasma membranes.

In view of the success of creating irreversible inhibitor of es transporter protein using cytidine as a lead compound, reproduction of the invention can be implemented by attaching a covalent arm to other physiological nucleosides such as adenosine (FIG. 17). $^3$H-Adenosine was chemically modified to incorporate various sulfhydryl reactive covalent arms onto the 6-amino position of the purine ring according to the general procedure set out in FIG. 3, and using the chemicals listed in Example 5. HL-60 plasma membranes were incubated with 100 μM of these chemically modified $^3$H-adenosine analogs for 5 min. The reaction was terminated by membrane filtration method. FIG. 17 shows 4-[p-maleimidophenyl]butyrylic acid (MPB) covalent arm promotes highest irreversible binding of $^3$H-adenosine (100 μM) to the HL-60 plasma membranes followed by N-α-maleimidoacetic acid (AMA). However, 3-[2-pyridyldithio]-propionic acid (PDP), N-ε-maleimidocaproylic acid (EMC), m-maleimidobenzoic acid (MB), and N-maleimidomethyl cyclohexane carboxylic acid (MCC) were equally lesser effective as covalent arms. In contrast, N-γ-maleimidobutyrylic acid (GMB) and α-methyl-α-[2-pyridyldithio]toluene carbonic acid (MPT) were least effective.

Example 8

Inhibitory Effects of Irreversible Interaction 5-HT Analogs on the Binding of $^3$H-5-HT in Murine Brain Membranes A. Compound Synthesis The compounds shown in FIGS. 19a, 20a, 21a and 22a (chemical structures of LBT3001 (1-[2-(5-hydroxy-1H-indol-3-yl)-ethyl]-pyrrole-2,5-dione), LBT3002 (4-(2,5-dioxo-2,5-dihydro-pyrrol-1-yl)-N-[2-(5-hydroxyl-1H-indol-3-yl)-ethyl]-butyramide), LBT3004 (3-(2,5-dioxo-2,5-dihydro-pyrrol-1-yl)-N-[2-(5-hydroxyl-1H-indol-3-yl)-ethyl]-propionamide), and LBT3005 (4-(2,5-dioxo-2,5-dihydro-pyrrol-1-yl-methyl)-cyclohexane carboxylic acid [2-(5-hydroxy-1H-indol-3-yl)-ethyl]-amide), respectively) demonstrated efficacy as irreversible binding compounds, and provide examples of modified ligands which are modified 5-HT receptor binding ligands comprising conjugation agents.

The reaction scheme for synthesis of LBT3001 (FIG. 19b) is as follows: 5-Hydroxytyptamine (212.7 mg, 1.0 mmol) was dissolved in saturated sodium bicarbonate (25 ml) solution at 0° C. N-Ethoxycarbonyleimide (177.6 mg, 1.05 mmol) was added under stirring. After 30 minutes, the ice-water bath was replaced with warm water bath (30° C. to 40° C.). The reaction solution was then stirred in the warm water bath for about one hour. The solution was then extracted with ethyl acetate (3×50 ml). The ethyl acetate layer was then washed with deionized water until pH close to neutral (2×20 ml) and then with brine (20 ml). The organic layer was then dried with anhydrous $MgSO_4$. The solvent was removed under reduced pressure to obtain a crude product in yellow oil. Purification through flash chromatography (30% ethyl acetate in hexane) afforded the product as a yellow to orange crystal (187.2 mg, 73%).

The reaction scheme for synthesis of LBT3002 (FIG. 20b) is as follows: 5-Hydroxytryptamine hydrochloride (42.5 mg, 0.2 mmol) and 3-maleimidobutyric acid (40.3 mg, 0.22 mmol) were suspended in 1 ml 2-methoxyethyl ether (DME). To the solution, N-methyl morpholine (NMM, 25 μl, 0.22 mmol) and 1,3-dicyclohexylcarbodiimide (DCC, 45.4 mg, 0.22 mmol) were added. The solution was stirred for 3 hours at the room temperature. The product was purified by flash chromatography directly using a gradient solvent eluent (0% to 3% methanol in methylene chloride) to generate brownish oil (40.7 mg, 60%).

The reaction scheme for synthesis of LBT3004 (FIG. 21b) is as follow: 5-Hydroxytryptamine hydrochloride (42.5 mg, 0.2 mmol) and 3-maleimidopropionic acid (37.2 mg, 0.22 mmol) were suspended in 1 ml methoxyethyl ether (DME). To the solution, N-methyl morpholine (NMM, 25 μl, 0.22 mmol) and 1,3-dicyclohexylcarbodiimide (DCC, 45.4 mg, 0.22 mmol) were added. The solution was stirred for 3 hours at the room temperature. The product was purified by flash chromatography directly using a gradient solvent eluent (0% to 1.5% to 5% methanol in methylene chloride) to generate an orange crystal (46.0 mg, 70%). The reaction scheme for synthesis of LBT3005 (FIG. 22b) is as follow: 4-Aminomethyl-cyclohexanecarboxylic acid (2.83 g, 18.0 mmol) in saturated $NaHCO_3$ (80 ml) was stirred vigorously at 0° C. To the solution, N-ethoxycarbonyleimide (finely grounded, 3.05 g, 18.0 mmol) was added portion by portion. When the addition was completed (c.a. 10 minutes), deionized water (80 ml) was added and the mixture was stirred at room temperature for 40 minutes. The resulting mixture was bought to pH 1–2 with 1 M of HCl and extracted with ethyl acetate (3×80 ml). The organic layer was washed with deionized water (50 ml) and then brine (20 ml). The organic phase was dried over magnesium sulfate and evaporated under reduced pressure to generate a crude product. Purification by flash chromatography (hexane:ethyl acetate:acetic acid, 60:39:1) to afford the product as a solid (2.69 g, 63%). 5-Hydroxytryptamine hydrochloride (42.5 mg, 0.2 mmol) and maleimidomethyl-cyclohexane carboxylic acid (52.2 mg, 0.22 mmol) were suspended in 1 ml methoxyethyl ether (DME). To the solution, N-methyl morpholine (NMM, 25 μl, 0.22 mmol) and 1,3-dicyclohexylcarbodiimide (DCC, 45.4 mg, 0.22 mmol) were added. The solution was stirred for 3 hours at the room temperature. The product was purified by flash chromatography directly using a gradient solvent eluent (ethyl acetate:hexane (1:1) to ethyl acetate:hexane (3:1)) to generate a light brown oil (28.3 mg, 35.8%). Other 5-HT receptor binding compounds such as those shown in FIG. 23 can be similarly modified for irreversible binding to their target sites using one of the reaction schemes illustrated in FIGS. 19b to 22b.

B. Assay

Figure 18:
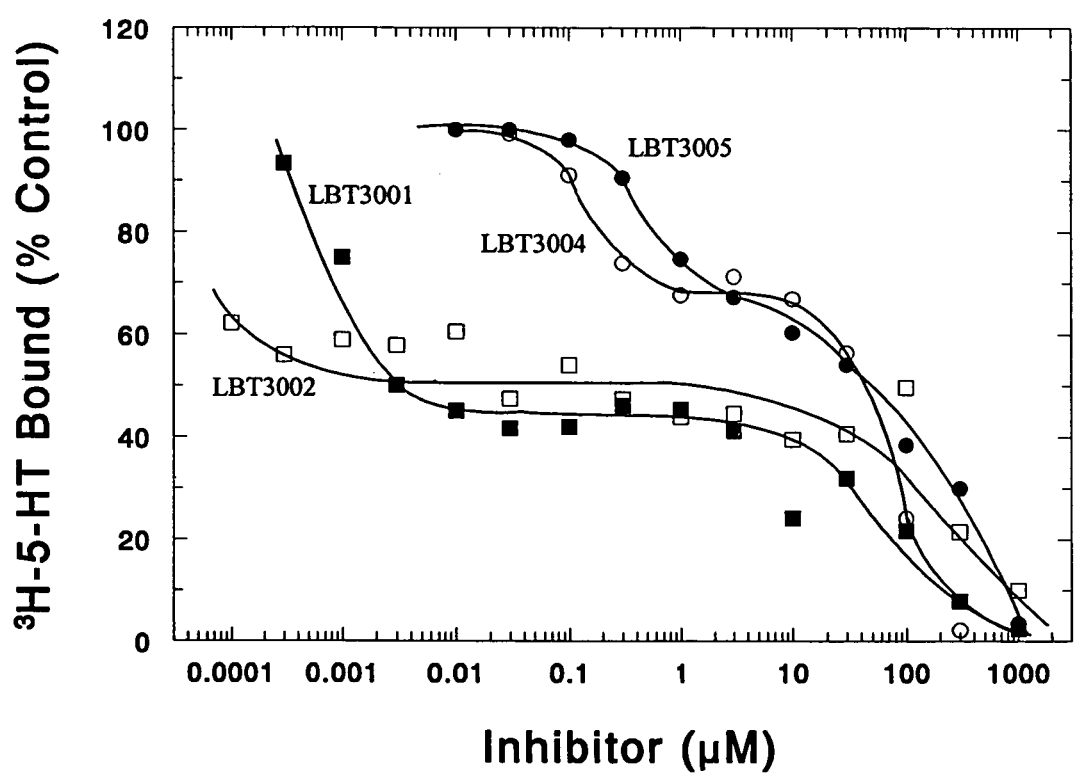
FIG. 18 shows the inhibition of $^3$H-5-HT binding to murine brain membranes by various 5-HT analogs.

FIG. 18 shows the inhibitory effects of various 5-HT analogs on the high affinity binding of $^3$H-5-HT to murine brain membranes. Purified murine brain membranes suspended in reaction buffer (0.13 M NaCl, 0.02 M $NaHCO_3$, pH 7.0) were pretreated with graded concentrations of LBT3001 (■), LBT3002 (□), LBT3004 (○), and LBT3005 (●) for 5 min prior exposure to $^3$H-5-HT (5 nM final concentration) for additional 30 min. The reaction was terminated by membrane vacuum filtration method. The data shown were corrected for non-specific binding determined in the presence of 1 mM of non-radioactive 5-HT. The results were plotted against control binding determined in the absence of inhibitors.

FIG. 18 shows the binding of $^3$H-5-HT to murine brain membranes was inhibited by all analogs of 5-HT in an apparent biphasic manner.

LBT3001 (1-[2-(5-hydroxy-1H-indol-3-yl)-ethyl]-pyrrole-2,5-dione), an analog containing no spacer arm between the 5-HT and the maleimide molecules (FIG. 19a), effectively inhibited the binding of $^3$H-5-HT to its high and low affinity binding sites with $IC_{50}$ values of about 0.001 and 50 μM, respectively. LBT3002, an analog containing 3 carbon molecules in the spacer arm (FIG. 20a), inhibited the binding of $^3$H-5-HT to its high and low affinity binding sites with $IC_{50}$ values of about 0.00003 and 200 μM, respectively. LBT3004, an analog containing 2 carbon molecules in the spacer arm (FIG. 21a), inhibited the binding of $^3$H-5-HT to its high and low affinity binding sites with $IC_{50}$ values of about 0.2 and 50 μM, respectively. LBT3005, an analog containing cyclohexane carboxylic molecule in the spacer arm (FIG. 22a), inhibited the binding of $^3$H-5-HT to its high and low affinity binding sites with $IC_{50}$ values of 0.5 and 300 μM, respectively. These results clearly indicate irreversible binding drugs can be designed using the technology described. Additionally, the technology is applicable to many small molecules and can be applied to further improve the efficacy of existing molecules.

The entire disclosures of all publications, patents and patent applications referred to herein are hereby incorporated by reference.

Throughout the specification the aim has been to describe the preferred embodiments of the invention without limiting the invention to any one embodiment or specific collection of features. Those of skill in the art will appreciate that, in light of the instant disclosure, various modifications and changes can be made in the particular embodiments exemplified without departing from the scope of the present invention. All such modifications and changes are intended to be included within the scope of the appendant claims.

The invention claimed is:

1. A modified ligand having a structure selected from the group consisting of the structures shown below:

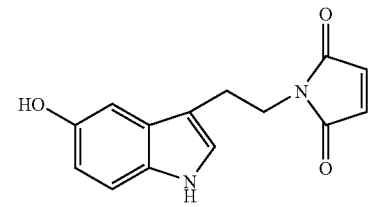

LBT3001 (1-[2-(5-hydroxy-1H-indol-3-yl)-ethyl]-pyrrole-2,5-dione)

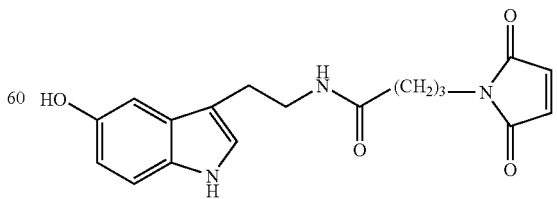

LBT3002 (4-(2,5-dioxo-2,5-dihydro-pyrrol-1-yl)-N-[2-(5-hydroxy-1H-indol-3-yl)-ethyl]-butyramide)

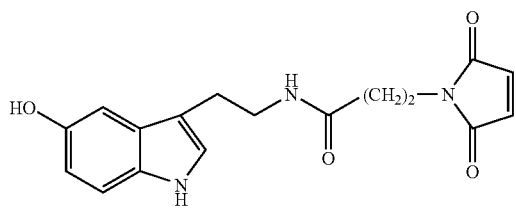

LBT3004 (3-(2,5-dioxo-2,5-dihydro-pyrrol-1-yl)-N-[2-(5-hydroxy-1H-indol-3-yl)-ethyl]-propionamide); and

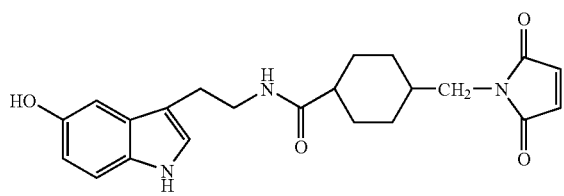

LBT3005 (4-(2,5-dioxo-2,5-dihydro-pyrrol-1-ylmethyl)-cyclohexane carboxylic acid [2-(5-hydroxy-1H-indol-3-yl)-ethyl]-amide).

2. A method of detecting the presence of a target serotonin receptor in a test sample, comprising: contacting said sample with the modified ligand of claim 1, wherein said modified ligand covalently binds said target receptor if present in said test sample; and detecting the presence of a complex comprising said modified ligand and said receptor in said contacted sample.

3. A method of quantifying the presence of a target serotonin receptor in a test sample, comprising: contacting said sample with the modified ligand of claim 1, wherein said modified ligand covalently binds said target receptor if present in said test sample; measuring the concentration of a complex comprising said modified ligand and said receptor in said contacted sample; and relating said measured complex concentration to the concentration of said receptor in said sample.

* * * * *